US007056741B2

(12) United States Patent
Uhler

(10) Patent No.: US 7,056,741 B2
(45) Date of Patent: Jun. 6, 2006

(54) SURFACE TRANSFECTION AND EXPRESSION PROCEDURE

(75) Inventor: Michael D. Uhler, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 439 days.

(21) Appl. No.: 10/002,802

(22) Filed: Nov. 2, 2001

(65) Prior Publication Data

US 2002/0197720 A1   Dec. 26, 2002

Related U.S. Application Data

(63) Continuation-in-part of application No. 09/960,454, filed on Sep. 21, 2001, now Pat. No. 6,897,067.

(60) Provisional application No. 60/305,552, filed on Jul. 13, 2001, provisional application No. 60/245,892, filed on Nov. 3, 2000.

(51) Int. Cl.
*C12N 15/88* (2006.01)
*C12N 15/63* (2006.01)
*C12M 1/02* (2006.01)

(52) U.S. Cl. .................... 435/458; 435/302; 435/320.1
(58) Field of Classification Search ................ 435/455, 435/458, 320.1, 395
See application file for complete search history.

(56) References Cited

U.S. PATENT DOCUMENTS

| | | | |
|---|---|---|---|
| 4,683,195 A | 7/1987 | Mullis et al. ................... 435/6 |
| 4,683,202 A | 7/1987 | Mullis et al. ................... 435/91 |
| 4,965,188 A | 10/1990 | Mullis et al. ................... 435/6 |
| 5,352,605 A | 10/1994 | Fraley et al. ............ 435/240.4 |
| 5,584,807 A | 12/1996 | McCabe ....................... 604/71 |
| 5,618,682 A | 4/1997 | Scheirer ........................ 435/8 |
| 5,654,185 A | 8/1997 | Palsson ................... 435/235.1 |
| 5,674,713 A | 10/1997 | McElroy et al. ........... 435/69.7 |
| 5,736,392 A * | 4/1998 | Hawley-Nelson et al. ........................ 435/320.1 |
| 5,804,431 A | 9/1998 | Palsson ................... 435/235.1 |
| 5,811,274 A | 9/1998 | Palsson ................... 435/172.2 |
| 5,837,533 A | 11/1998 | Boutin .................... 435/320.1 |
| 5,965,352 A | 10/1999 | Stoughton ............... 435/172.1 |
| 5,972,900 A * | 10/1999 | Perkol, Jr. et al. ............. 514/44 |
| 5,976,796 A | 11/1999 | Szalay et al. ................... 435/6 |
| 5,998,136 A | 12/1999 | Kamb ............................ 435/6 |
| 6,060,240 A | 5/2000 | Kamb et al. ................... 435/6 |
| 6,074,859 A | 6/2000 | Hirokawa et al. ........... 435/189 |
| 6,077,834 A * | 6/2000 | Cheng .......................... 514/44 |
| 6,544,790 B1 | 4/2003 | Sabatini ...................... 435/455 |

FOREIGN PATENT DOCUMENTS

| | | |
|---|---|---|
| EP | 0900849 | 3/1999 |
| WO | WO 95/14098 | 5/1995 |
| WO | WO 97/18317 * | 5/1997 |
| WO | WO 97/49434 * | 12/1997 |
| WO | WO 98/53103 | 11/1998 |
| WO | WO 99/51773 | 10/1999 |
| WO | WO 99/55886 | 11/1999 |
| WO | WO 99/58664 | 11/1999 |
| WO | WO 00/05339 | 2/2000 |
| WO | WO 01/20015 | 3/2001 |

OTHER PUBLICATIONS

Wagner et al. Transferrin-polycation conjugates as carriers for DNA uptake into cells. Proc. Natl. Acad. Sci. USA 87:3410-3414, 1990.*
U.S. Appl. No. 10/002,802, Uhler et al.
U.S. Appl. No. 10/123,435, Uhler et al.
Amundson, et al., Fluorescent cDNA microarray hybridization reveals complexity and heterogeneity of cellular genotoxic stress responses, Oncogene, 18(24):3666 (1999).
Bally, et al., Biological barriers to cellular delivery of lipid-based DNA carriers, Adv Drug Deliv Rev, 38(3):291 (1999).
Baron, et al., Generation of conditional mutants in higher eukaryotes by switching between the expression of two genes, Proc Natl Acad Sci U S A, 96(3):1013 (1999).
Bittner, et al., Data analysis and integration: of steps and arrows, Nat Genet, 22(3):213 (1999).
Boynton and AL., Control of 3T3 cell proliferation by calcium, In Vitro, 10(12 (1974).
Brown and Botstein, Exploring the new world of the genome with DNA microarrays, Nat Genet, 21(1 Suppl):33 (1999).
Brown, et al., Induction of alkaline phosphatase in mouse L cells by overexpression of the catalytic subunit of cAMP-dependent protein kinase, J Biol Chem, 265(22):13181 (1990).
Brunner, et al., Cell cycle dependence of gene transfer by lipoplex, polyplex and recombinant adenovirus, Gene Ther, 7(5):401 (2000).
Cheng, Receptor ligand-facilitated gene transfer: enhancement of liposome-mediated gene transfer and expression by transferrin, Hum Gene Ther, 7(3):275 (1996).
Duggan, et al., Expression profiling using cDNA microarrays, Nat Genet, 21(1 Suppl):10 (1999).

(Continued)

*Primary Examiner*—David Guzo
*Assistant Examiner*—Quang Nguyen
(74) *Attorney, Agent, or Firm*—Medlen & Carroll, LLP

(57) ABSTRACT

The present invention relates to a method of transfecting cells comprising applying cells directly onto nucleic acids which are immobilized in transfection complexes on a surface and which transfect the cells. Preferably, the nucleic acids are immobilized in an array. In another aspect of the present invention, the method further includes expression of the nucleic acids in the transfected cells. In yet another aspect of the present invention, the method further comprises detecting the expression of the nucleic acids in the transfected cells.

21 Claims, 4 Drawing Sheets

OTHER PUBLICATIONS

Gill and Sanseau, Rapid in silico cloning of genes using expressed sequence tags (ESTs), Biotechnol Annu Rev, 5(25 (2000).

Graves, Powerful tools for genetic analysis come of age, Trends Biotechnol, 17(3):127 (1999).

Huang, et al., Identification and temporal expression pattern of genes modulated during irreversible growth arrest and terminal differentiation in human melanoma cells, Oncogene, 18(23):3546 (1999).

Iyer, et al., The transcriptional program in the response of human fibroblasts to serum, Science, 283(5398):83 (1999).

Mann, et al., Pressure-mediated oligonucleotide transfection of rat and human cardiovascular tissues, Proc Natl Acad Sci U S A, 96(11):6411 (1999).

Mortimer, et al., Cationic lipid-mediated transfection of cells in culture requires mitotic activity, Gene Ther, 6(3):403 (1999).

Neumann, et al., Fundamentals of electroporative delivery of drugs and genes, Bioelectrochem Bioenerg, 48(1):3 (1999).

Ross, et al., Enhanced reporter gene expression in cells transfected in the presence of DMI-2, an acid nuclease inhibitor, Gene Ther, 5(9):1244 (1998).

Schena, et al., Quantitative monitoring of gene expression patterns with a complementary DNA microarray, Science, 270(5235):467 (1995).

Tseng, et al., Mitosis enhances transgene expression of plasmid delivered by cationic liposomes, Biochim Biophys Acta, 1445(1):53 (1999).

Wagner, et al., DNA-binding transferrin conjugates as functional gene-delivery agents: synthesis by linkage of polylysine or ethidium homodimer to the transferrin carbohydrate moiety, Bioconjug Chem, 2(4):226 (1991).

Watson and Akil, Gene chips and arrays revealed: a primer on their power and their uses, Biol Psychiatry, 45(5):533 (1999).

Young, Biomedical discovery with DNA arrays, Cell, 102(1):9 (2000).

Zenke, et al., Receptor-mediated endocytosis of transferrin-polycation conjugates: an efficient way to introduce DNA into hematopoietic cells, Proc Natl Acad Sci U S A, 87(10):3655 (1990).

Zhu, et al., Cellular gene expression altered by human cytomegalovirus: global monitoring with oligonucleotide arrays, Proc Natl Acad Sci U S A, 95(24):14470 (1998).

Antonyak, et al., Constitutive activation of c-Jun N-terminal kinase by a mutant epidermal growth factor receptor, J Biol Chem, 273(5):2817 (1998).

Barila, et al., A nuclear tyrosine phosphorylation circuit: c-Jun as an activator and substrate of c-Abl and JNK, Embo J, 19(2):273 (2000).

Collins and Uhler, Cyclic AMP- and cyclic GMP-dependent protein kinases differ in their regulation of cyclic AMP response element-dependent gene transcription, J Biol Chem, 274(13):8391 (1999).

Frodin, et al., A phosphoserine-regulated docking site in the protein kinase RSK2 that recruits and activates PDK1, Embo J, 19(12):2924 (2000).

Frost, et al., Cross-cascade activation of ERKs and ternary complex factors by Rho family proteins, Embo J, 16(21):6426 (1997).

Fuchs, et al., MEKK1/JNK signaling stabilizes and activates p53, Proc Natl Acad Sci U S A, 95(18):10541 (1998).

Gryz and Meakin, Acidic substitution of the activation loop tyrosines in TrkA supports nerve growth factor-independent cell survival and neuronal differentiation, Oncogene, 19(3):417 (2000).

Guan, et al., Interleukin-1beta-induced cyclooxygenase-2 expression requires activation of both c-Jun NH2-terminal kinase and p38 MAPK signal pathways in rat renal mesangial cells, J Biol Chem, 273(44):28670 (1998).

Hansra, et al., Multisite dephosphorylation and desensitization of conventional protein kinase C isotypes, Biochem J, 342 (Pt 2)(337 (1999).

Huggenvik, et al., Regulation of the human enkephalin promoter by two isoforms of the catalytic subunit of cyclic adenosine 3',5'-monophosphate-dependent protein kinase, Mol Endocrinol, 5(7):921 (1991).

Iglesias and Rozengurt, Protein kinase D activation by deletion of its cysteine-rich motifs, FEBS Lett, 454(1-2):53 (1999).

Kawai, et al., Mouse smad8 phosphorylation downstream of BMP receptors ALK-2, ALK-3, and ALK-6 induces its association with Smad4 and transcriptional activity, Biochem Biophys Res Commun, 271(3):682 (2000).

Kohn, et al., Expression of a constitutively active Akt Ser/Thr kinase in 3T3-L1 adipocytes stimulates glucose uptake and glucose transporter 4 translocation, J Biol Chem, 271(49):31372 (1996).

Komeima, et al., Inhibition of neuronal nitric-oxide synthase by calcium/calmodulin-dependent protein kinase IIalpha through Ser847 phosphorylation in NG108-15 neuronal cells, J Biol Chem, 275(36):28139 (2000).

Kuno-Murata, et al., Augmentation of thyroid hormone receptor-mediated transcription by Ca2+/calmodulin-dependent protein kinase type IV, Endocrinology, 141(6):2275 (2000).

Leevers, et al., Requirement for Ras in Raf activation is overcome by targeting Raf to the plasma membrane, Nature, 369(6479):411 (1994).

Ling, et al., NF-kappaB-inducing kinase activates IKK-alpha by phosphorylation of Ser-176, Proc Natl Acad Sci U S A, 95(7):3792 (1998).

Novak, et al., Cell adhesion and the integrin-linked kinase regulate the LEF-1 and beta-catenin signaling pathways, Proc Natl Acad Sci U S A, 95(8):4374 (1998).

Ohteki, et al., Negative regulation of T cell proliferation and interleukin 2 production by the serine threonine kinase GSK-3, J Exp Med, 192(1):99 (2000).

Raingeaud, et al., MKK3- and MKK6-regulated gene expression in mediated by the p38 mitogen-activated protein kinase signal transduction pathway, Mol Cell Biol, 16(3):1247 (1996).

Robinson, et al., A constitutively active and nuclear form of the MAP kinase ERK2 is sufficient for neurite outgrowth and cell transformation, Curr Biol. 8(21):1141 (1998).

Takeda, et al., Apoptosis signal-regulating kinase 1 (ASK1) induces neuronal differentiation and survival of PC12 cells, J Biol Chem, 275(13):9805 (2000).

Wang, et al., Activation of the hematopoietic progenitor kinase-1 (HPK1)-dependent, stress-activated c-Jun N-terminal kinase (JNK) pathway by transforming growth factor beta (TGF-beta)-activated kinase (TAK1), a kinase mediator of TGF beta signal transduction, J Biol Chem, 272(36):22771 (1997).

Zang, et al., Association between v-Src and Protein kinase C delta in v-Src-transformed fibroblasts, J Biol Chem, 272(20):13275 (1997).

Zimmermann, et al., PrKX is a novel catalytic subunit of the cAMP-dependent protein kinase regulated by the regulatory subunit type I, J Biol Chem, 274(9):5370 (1999).

Abravaya, et al., Heat shock-induced interactions of heat shock transcription factor and the human hsp70 promoter examined by in vivo footprinting, Mol Cell Biol, 11(1):586 (1991).

Altmann, et al., Transcriptional activation by CTF proteins is mediated by a bipartite low-proline domain, Proc Natl Acad Sci U S A, 91(9):3901 (1994).

Benbrook and Jones, Different binding specificities and transactivation of variant CRE's by CREB complexes, Nucleic Acids Res, 22(8):1463 (1994).

Blackwell, et al., Sequence-specific DNA binding by the c-Myc protein, Science, 250(4984):1149 (1990).

Boccaccio, et al., Induction of epithelial tubules by growth factor HGF depends on the STAT pathways, Nature, 391(6664):285 (1998).

Cao, et al., Identification and characterization of the Egr-1 gene product, a DNA-binding zinc finger protein induced by differentiation and growth signals, Mol Cell Biol, 10(5):1931 (1990).

Fisch, et al., An AP1-binding site in the c-fos gene can mediate induction by epidermal growth factor and 12-O-tetradecanoyl phorbol-13-acetate, Mol Cell Biol, 9(3):1327 (1989).

Hale and Braithwaite, Identification of an upstream region of the mouse p53 promoter critical for transcriptional expression, Nucleic Acids Res, 23(4):663 (1995).

Hariharan, et al., Delta, a transcription factor that binds to downstream elements in several polymerase II promoters, is a functionally versatile zinc finger protein, Proc Natl Acad Sci U S A, 88(21):9799 (1991).

Hiscott, et al., Triggering the interferon response: the role of IRF-3 transcription factor, J Interferon Cytokine Res, 19(1):1 (1999).

Kamps, et al., A new homeobox gene contributes the DNA binding domain of the t(1;19) translocation protein in pre-B ALL, Cell, 60(4):547 (1990).

Lam, et al., Cell-cycle regulation of human B-myb transcription, Gene, 160(2):277 (1995).

Lernbecher, et al., Distinct NF-kappa B/Rel transcription factors are responsible for tissue-specific and inducible gene activation, Nature, 365(6448):767 (1993).

Northrop, et al., Characterization of the nuclear and cytoplasmic components of the lymphoid-specific nuclear factor of activated T cells (NF-AT) complex, J Biol Chem, 268(4):2917 (1993).

Oh and Im, The p53 mutation which abrogates trans-activation while maintaining its growth-suppression activity, Mol Cells, 10(4):386 (2000).

Pani, et al., The restricted promoter activity of the liver transcription factor hepatocyte nuclear factor 3 beta involves a cell-specific factor and positive autoactivation, Mol Cell Biol, 12(2):552 (1992).

Robbins, et al., Negative regulation of human c-fos expression by the retinoblastoma gene product, Nature, 346(6285):668 (1990).

Treisman, The SRE: a growth factor responsive transcriptional regulator, Semin Cancer Biol, 1(1):47 (1990).

Uchijima, et al., Tax proteins of human T-cell leukemia virus type 1 and 2 induce expression of the gene encoding erythroid-potentiating activity (tissue inhibitor of metalloproteinases-1, TIMP-1), J Biol Chem, 269(21):14946 (1994).

Vinson, et al., Dimerization specificity of the leucine zipper-containing bZIP motif on DNA binding: prediction and rational design, Genes Dev, 7(6):1047 (1993).

Ziauddin, J and Sabatini, DM (2001) Microarrays of cells expressing defined cDNAs. Nature 411:107-110.

Wagner, et al. (1992) Influenza virus hemagglutinin HA-2 N-terminal fusogenic peptides augment gene transfer by transferrin-polylysine-DNA complexes: toward a synthetic virus-like gene-transfer vehicle, Proc Natl Acad Sci U S A, 89(17):7934.

* cited by examiner

SEQUENCE LISTING

<160> NUMBER OF SEQ ID NOS: 22

<210> SEQ ID NO 1
<211> LENGTH: 20
<212> TYPE: DNA
<213> ORGANISM: Homo sapiens

<400> SEQUENCE: 1
gttctcgctg gtgagtttca                    20

<210> SEQ ID NO 2
<211> LENGTH: 7
<212> TYPE: DNA
<213> ORGANISM: Homo sapiens

<400> SEQUENCE: 2 tgactca                                   7

<210> SEQ ID NO 3
<211> LENGTH: 8
<212> TYPE: DNA
<213> ORGANISM: Mus musculus

<400> SEQUENCE: 3 tgacgtca                                  8

<210> SEQ ID NO 4
<211> LENGTH: 9
<212> TYPE: DNA
<213> ORGANISM: Homo sapiens

<400> SEQUENCE: 4 gggaattcc                                 9

<210> SEQ ID NO 5
<211> LENGTH: 12
<212> TYPE: DNA
<213> ORGANISM: Rattus norvegicus -continued

```
<400> SEQUENCE: 5
gaaactgaaa ct                                                          12

<210> SEQ ID NO 6
<211> LENGTH: 12
<212> TYPE: DNA
<213> ORGANISM: Homo sapiens

<400> SEQUENCE: 6
aaactgaaac tg                                                          12

<210> SEQ ID NO 7
<211> LENGTH: 22
<212> TYPE: DNA
<213> ORGANISM: Homo sapiens

<400> SEQUENCE: 7
agtttcatat ttactctaaa tc                                               22

<210> SEQ ID NO 8
<211> LENGTH: 29
<212> TYPE: DNA
<213> ORGANISM: Rattus norvegicus

<400> SEQUENCE: 8
ggaggaaaaa ctgttcatac agaaggcgt                                        29

<210> SEQ ID NO 9
<211> LENGTH: 12
<212> TYPE: DNA
<213> ORGANISM: Homo sapiens

<400> SEQUENCE: 9
cacgtccacg tc                                                          12

<210> SEQ ID NO 10
<211> LENGTH: 17
<212> TYPE: DNA
<213> ORGANISM: Homo sapiens

<400> SEQUENCE: 10
cttggcggga gatagaa                                                     17

<210> SEQ ID NO 11
<211> LENGTH: 8
<212> TYPE: DNA
<213> ORGANISM: Mus musculus

<400> SEQUENCE: 11 ccaggaag                                                                8

<210> SEQ ID NO 12
<211> LENGTH: 13
<212> TYPE: DNA
<213> ORGANISM: Rattus norvegicus

<400> SEQUENCE: 12
atgcaaatga tat                                                         13

<210> SEQ ID NO 13
<211> LENGTH: 13
<212> TYPE: DNA
<213> ORGANISM: Mus musculus
```

```
<400> SEQUENCE: 13
ctaagtcaat aat                                                    13

<210> SEQ ID NO 14
<211> LENGTH: 20
<212> TYPE: DNA
<213> ORGANISM: Mus musculus

<400> SEQUENCE: 14
tgcagattgc gcaatctgca                                             20

<210> SEQ ID NO 15
<211> LENGTH: 16
<212> TYPE: DNA
<213> ORGANISM: Homo sapiens

<400> SEQUENCE: 15
gccagccaat gagcgc                                                 16

<210> SEQ ID NO 16
<211> LENGTH: 21
<212> TYPE: DNA
<213> ORGANISM: Mus musculus

<400> SEQUENCE: 16
cgccctcgcc cccgcgccgg g                                           21

<210> SEQ ID NO 17
<211> LENGTH: 13
<212> TYPE: DNA
<213> ORGANISM: Homo sapiens

<400> SEQUENCE: 17
ccccgctgcc atc                                                    13

<210> SEQ ID NO 18
<211> LENGTH: 25
<212> TYPE: DNA
<213> ORGANISM: Homo sapiens

<400> SEQUENCE: 18
gttatggcga ctatccagct ttgtg                                       25

<210> SEQ ID NO 19
<211> LENGTH: 23
<212> TYPE: DNA
<213> ORGANISM: Rattus norvegicus

<400> SEQUENCE: 19 gaaaccctg gaatattccc gac                                          23

<210> SEQ ID NO 20
<211> LENGTH: 9
<212> TYPE: DNA
<213> ORGANISM: Rattus norvegicus

<400> SEQUENCE: 20 ttcccgtaa                                                          9

<210> SEQ ID NO 21
<211> LENGTH: 22
<212> TYPE: DNA
```

```
-continued

<213> ORGANISM: Human cytomegalovirus

<400> SEQUENCE: 21
attacggggt cattagttca ta                                              22

<210> SEQ ID NO 22
<211> LENGTH: 22
<212> TYPE: DNA
<213> ORGANISM: Simian virus 40

<400> SEQUENCE: 22
tctcggtcta ttcttttgat tt                                              22
```

Surface Transfection and Expression Procedure

Microarray of spots of nucleic acid in compatible host cell expression vector

↓ Plating of adherent cells onto microarrayed spots followed by incubation

Detection of desired spot by fluorescence (●), autoradiographic assay, absorbance, etc.

SURFACE TRANSFECTION AND EXPRESSION PROCEDURE

This is a Continuation In-Part of application(s) 60/245,892 filed on Nov. 3, 2000 and 60/305,552 filed on Jul. 13, 2001 and Ser. No. 09/960,454 filed on Sep. 21, 2001 now U.S. Pat. No. 6,897,067.

FIELD OF THE INVENTION

The present invention relates to a method of cell transfection, and in particular to the application of cells to nucleic acids which are immobilized on a surface and which then transfect the cells. In one embodiment, the nucleic acids are immobilized in an array.

BACKGROUND OF THE INVENTION

The wealth of information generated by the Human Genome Project and other genome projects has spurred research in many traditional disciplines such as cell biology and has given birth to entirely new disciplines such as bioinformatics and proteomics. The functional analysis of the nucleotide information provided by the Human Genome Project will fuel research questions over the next several decades and complete sequence determination of the human genome should be publicly available by 2003. This first step in characterization of the human genome presents tremendous opportunities to understand the function of these genes.

An important extension of the various genome sequencing projects has been the sequencing of short sequences of nucleotides at the 5' and 3' ends of cDNA clones and the generation of expressed sequence tag (EST) sequences for comparison with the sequences obtained from genomic DNA (Gill and Sanseau (2000) Biotechnol Annu Rev 5:25–44). The presence of sequences within an EST database demonstrates that some portion of the gene is transcribed into mRNA in a particular cell and at some relative level of abundance. The sequencing of ESTs has provided substantial insight into the tissue specific and pathological regulation of gene expression. For many individual biomedical researchers, the partial characterization of ESTs has greatly facilitated the cloning and expression of genes of interest since many of the ESTs are readily available from public or commercial sources.

A number of techniques currently under development to understand the regulation of gene expression take advantage of the large genomic databases and the availability of ESTs. One such major new technology is the use of DNA microarrays to study regulation of gene transcription by quantifying gene expression (Bittner et al. (1999) Nat Genet. 22(3): 213–215; Graves D J (1999) Trends Biotechnol. 17(3): 127–34; Watson and Akil (1999) Biol Psychiatry 45:533–543; Brown and Botstein (1999) Nat Genet 21:33–37; Duggan et al. (1999) Nat Genet 21:10–14; Young (2000) Cell 102:9–15). In this approach, very small amounts of DNA are applied to the surface of glass microscope slides (Schena et al (1995) Science 270: 467–470). Typically, the DNA sample is a short PCR-amplified fragment corresponding to a known gene or EST sequence. Approximately 100 nanoliters of DNA solution containing 10 ng of DNA is applied and fixed to the glass slide. The application of DNA can be automated and robotic devices can spot 10,000 individual DNA samples onto a single microscope slide in arrays of easily identifiable patterns. Since the entire process is robotic, it is possible to make tens or hundreds of replicates of such slides. For the analysis of gene expression, the slides are hybridized with fluorescently labeled cDNA derived from mRNA preparations obtained from various samples. After washing, the amount of fluorescent DNA hybridized to the glass slide is indicative of the amount of mRNA complementary to the individual PCR fragment. The fluorescence intensity is quantitated using an array scanner to determine the fluorescence signal at the wavelengths of the fluorophores used to label the cDNA.

This technique has been applied to the characterization of the transcriptional response of 8,600 individual genes in fibroblasts following serum stimulation (Iyer et al., 1999), and to the effect of viral infection, ionizing radiation, and cancer chemotherapeutic agents on transcriptional regulation (Brown and Botstein (1999) Nat Genet 21:33–37; Zhu H et al. (1998) Proc Natl Acad Sci U.S.A. 95(24):14470–5; Amundson S A et al. (1999) Oncogene 18(24):3666–72; Huang F et al. (1999) Oncogene 18(23):3546–52).

Despite the wealth of information which potentially can be generated using arrayed DNA sequences, the information is limited to detecting the presence of nucleic acid sequences which are already present within a cell. Thus, DNA microarrays are currently used to determine gene expression. Once changes in transcription have been characterized, information about the relevant EST sequences is often limited to searching for homology to other known genes; even if such homology exists, the functionality of proteins encoded by the sequences is not known but can only be inferred. Thus, current methodologies are limited, as they do not provide any insight in the function of a particular gene, particularly those which encode proteins which do not show significant homology to known genes. Essential information for determining protein function, particularly of uncharacterized genes, requires expression of the protein and its characterization. An even greater limitation of the current techniques which employ microarrayed DNA is that major aspects of cellular regulation can not determined using such techniques, since most regulation of cell function occurs by modification of existing protein structure rather than by regulation of gene transcription.

What is needed is the development of a high throughput screening assay for functional characterization of gene products; preferably, such a technique would also take advantage of the advances in DNA microarray technology.

SUMMARY OF THE INVENTION

Typically, determination of gene function involves transfection of cells with a gene under investigation. Currently, cell transfection is practiced by the addition of nucleic acid complexes to the media in which cells are grown; thus, there is no spatial restriction on the nucleic acid complexes which transfect the cells. It is an object of the present invention to provide a method that allows the functional characterization of proteins but that also takes advantage of the technological advances developed for DNA microarray hybridization.

These objectives are met by the present invention, which provide a novel transfection method in which nucleic acids are spatially restricted before and at the initiation of transfection. Thus, the present invention provides a method in which cells are plated directly onto immobilized nucleic acids and transfected by the immobilized nucleic acids. The nucleic acids are immobilized on a surface on which the cells can be grown, and are restricted to the original area of immobilization under normal cell culture conditions. In some aspects of the present invention, the spatial arrangement of the nucleic acids is an array; in preferred embodiments, the array is a microarray. In some embodiments, the array is an ordered array; in other embodiments, the array is a random array. In preferred embodiments of the present invention, the microarrays are generated by DNA arrayers, which are readily commercially available.

In one aspect, the method of the present invention further provides expression of the transfected nucleic acid; in yet an additional aspect, the method of the present further comprises detection of the expressed transfected nucleic acids. In this additional aspect of the present invention, the effects of transfected nucleic acids are easily measured, as for example by using appropriate fluorescent reporter constructs in the transfected cells, and detecting the fluorescence with commercially available scanners. The nucleic acids include, without being limited to, ESTs, PCR products, genomic DNA, cDNA, RNA, oligonucleotides and antisense constructs; such nucleic acids may be present within expression vectors. The present invention in its different aspects is referred to as Surface Transfection and Expression Procedure (STEP).

Currently, STEP is immediately applicable to the numerous existing sets of ESTs, many of which are in eukaryotic expression vectors. Moreover, STEP can be utilized to take advantage of antisense techniques so that the function of a protein can be studied without the availability of a full-length cDNA. Like the differential hybridization to EST arrays, STEP is widely applicable to a variety of cellular regulation pathways and is an important and useful technique to bridge genomics and proteomics.

Thus, the present invention provides a method of transfecting cells, comprising providing a transfection complex immobilized on a surface, the complex comprising nucleic acid and at least one complexing agent, and a cell; and contacting the cell with the nucleic acid in the immobilized transfection complex under conditions such that the cell is transfected. In some embodiments, the complexing agents are selected from the group consisting of ligands for receptors, DNA-binding molecules, and membrane permeable molecules. In other embodiments, the transfection complex comprises a first and second complexing agents, the first complexing agent comprising a ligand for receptors and the second complexing agent comprising a DNA binding protein; in yet other embodiments, the transfection complex further comprises a third complexing agent, the third complexing agent comprising a membrane permeable molecule. In some preferred embodiments, the ligand is for a receptor which is endocytosed by cells, the DNA binding molecule is a cationic protein, and the membrane permeable molecule is a cationic lipid. In other preferred embodiments, the first complexing agent comprises transferrin and the second complexing agent comprises polylysine. In other preferred embodiments, the first complexing agent comprises viral protein, and the second complexing agent comprises polylysine or a histone; in even more preferred embodiments, the viral protein is selected from the group consisting of penton protein, HIV protein GP120, equine rhinitis A virus protein VP1, human adenovirus protein E3, and Epstein-Barr virus protein GP350. In other embodiments, the transfection complex comprises at least two complexing agents, wherein at least two of the complexing agents are covalently linked to each other. In some preferred embodiments, the complexing agents comprise a ligand covalently linked to a cationic protein; in other preferred embodiments, the complexing agents comprise transferrin covalently linked to polylysine; in yet other preferred embodiments, the complexing agents comprise a viral protein covalently bound to polylysine or a histone. In yet other preferred embodiments, the transfection complex further comprises a third complexing agent, the third complexing agent comprising a membrane permeable molecule, which is preferably a cationic lipid. In yet other preferred embodiments, the complexing agents comprise transferrin, polylysine, and Lipofectamine®, wherein transferrin is covalently linked to polylysine. In other embodiments, the transfection complex further comprises at least one additional agent selected from the group consisting of targeting molecules, transcription molecules, nucleic acid degradation inhibitors, and cell growth and integrity modulators. In other embodiments, the nucleic acids are selected from the group consisting of ESTs, PCR products, genomic DNA, cDNA, RNA, oligonucleotides and antisense constructs; such nucleic acids may be present within expression vectors. In yet a further embodiment, at least one transfection complex comprises one type of nucleic acids. In another embodiment, at least one transfection complex comprises more than one type of nucleic acids.

In another aspect of the present invention, the immobilized transfection complexes form an array of surface immobilized transfection complexes, wherein the transfection complexes comprise nucleic acids and at least one complexing agent. In some embodiments, the array is a microarray. In some embodiments, the array is ordered; in other embodiments, the array is random. In yet another aspect, the surface has a configuration selected from the group consisting of flat, concave, convex, spherical, and cubical. In some embodiments, the surface is a multiwell tissue culture plate; in preferred embodiments, the surface is a 96 well or 384 well plate. In yet a further aspect, the surface is selected from the group consisting of a slide, a bead, a cube, a chip, a cube, a film, and a membrane. In another aspect of the present invention, the surface is made from a material selected from the group consisting of glass, plastic, films and membranes. In another aspect of the present invention, the surface is precoated with a compound to which both the nucleic acids and the cells adhere. In one embodiment, the compound is selected from the group consisting of polylysine, fibronectin, and lamenin.

In other embodiments of the invention, the cells are eukaryotic cells. In some embodiments, the cells are mammalian cells. In other embodiments, the cells are selected from the group consisting of cultured cells and cells freshly obtained from a source. In yet other embodiments, the cells are cultured cells which are selected from the group consisting of primary cultures, cell lines, and three-dimensional cultured cells. In yet further embodiments, the cells are in vivo; the cells may be selected from the group consisting of tissue cells, organ cells, and tumor cells.

In another aspect of the present invention, the method further comprises the step of expressing the nucleic acids in the transfected cells. In a further aspect of the present invention, the method further comprises the step of detecting the expression of the nucleic acids in the transfected cells. In some embodiments, detecting the expression is monitored over a period of time. In other embodiments, detecting the expression is assayed in intact cells. In other embodiments, the nucleic acids encode at least one fluorescent reporter protein, and expression is detected by fluorescence microscopy. In yet other embodiments, the nucleic acids encode at least one luminescent reporter protein, and expression is detected by a light detector.

The present invention also provides a method of transfecting a cell, comprising immobilizing a transfection complex on a surface, the complex comprising nucleic acid and at least one complexing agent, and contacting the cell with the immobilized nucleic acid in the transfection complex on the surface under conditions such that cells are transfected.

The embodiments of the transfection complex, the form of the complexes immobilized on the surface, the surface, and the cells are as described above. In another aspect of the present invention, the method further comprises the step of expressing the nucleic acid in the transfected cells, and in a further aspect of the present invention, the method further comprises the step of detecting the expression of the nucleic acid in the transfected cells, with the embodiments as described above.

The invention also provides a method of transfecting a cell, comprising combining nucleic acid with at least one complexing agent so as to form at least one transfection complex comprising the nucleic acid and the complexing agent; immobilizing the at least one transfection complex on a surface so as to form immobilized nucleic acid; and contacting a cell with the immobilized nucleic acid under conditions such that the cell is transfected. The embodiments of the transfection complex, the form of the transfection complexes immobilized on the surface, the surface, and the cells are as described above. In another aspect of the present invention, the method further comprises the step of expressing the nucleic acid in the transfected cell, and in a further aspect of the present invention, the method further comprises the step of detecting the expression of the nucleic acids in the transfected cell, with the embodiments as described above.

The present invention also provides a method of transfecting a cell, comprising covalently linking transferrin to polylysine; combining nucleic acid and at least one cationic lipid with the covalently linked polylysine and transferrin so as to form a transfection complex; immobilizing the transfection complex on a surface so as to form immobilized nucleic acid; and contacting the cell with the immobilized nucleic acid so as to create a transfected cell. In further aspects of the invention, the method further comprises expressing the nucleic acid in the transfected cells; and in yet further aspects of the invention, the method further comprises the step of detecting the expression of the nucleic acids in the transfected cells. The embodiments of the transfection complexes, the form of the nucleic acids immobilized on the surface, the surface, and the cells are as described above.

The present invention also provides a method of transfecting a cells, comprising providing transfection complexes immobilized on a surface in a random array, where the transfection complex comprises nucleic acid and at least one complexing agent, and a cell; and contacting the cell with the immobilized nucleic acids under conditions such that the cells is transfected. The embodiments of the transfection complexes, the form of the nucleic acids immobilized on the surface, the surface, and the cells are as described above. In another aspect of the present invention, the method further comprises the step of expressing the nucleic acid in the transfected cell, and in a further aspect of the present invention, the method further comprises the step of detecting the expression of the nucleic acid in the transfected cell, with the embodiments as described above.

Another aspect of the present invention provides a method of immobilizing nucleic acid to a surface, comprising combining the nucleic acid with at least one complexing agent so as to form at least one transfection complex; and contacting the at least one transfection complex to the surface under conditions sufficient to immobilize the nucleic acid. The embodiments of the transfection complexes, the form of the nucleic acids immobilized on the surface, and the surface are as described above. The present invention also provides a surface comprising immobilized nucleic acids, wherein the nucleic acid is immobilized in at least one transfection complex, produced by any of the methods described above. Thus, in some embodiments, the surface comprises immobilized nucleic acids in an array of surface immobilized nucleic acids; in some preferred embodiments, the array is a microarray. In some embodiments, the array is ordered; in other embodiments, the array is random. The embodiments of the transfection complexes and the surface are as described above.

In another aspect, the present invention also provides a transfection complex produced by any of the methods as described above. The present invention also provides a composition comprising any one or more of the transfection complexes described above. The present invention further provides a kit comprising in one or more containers any one or more of the transfection complexes described above.

The present invention also provides further aspects, in which a transfection complex of the present invention is employed in any of several applications; several of these aspects are described in the following paragraphs. In these further aspects, the embodiments of the transfection complex, complexing agents, nucleic acids, immobilization of the transfection complex to a surface, a surface, and a cell are generally as described above.

In another aspect, the present invention provides a method of a detecting a protein-protein binding pair, comprising: providing a transfection complex comprising a first and a second nucleic acid and at least one complexing agent, wherein the first nucleic acid encodes a first protein and wherein the second nucleic acid encodes a second protein, and the nucleic acids are present in at least one expression vector, and a cell; contacting the cell with the immobilized nucleic acids under conditions such that the cell is co-transfected with the first and the second nucleic acids and the first and the second nucleic acids are expressed; and detecting the presence of a protein-protein complex, wherein at least one protein is a protein encoded by at least one of the nucleic acids.

In yet another aspect, the present invention provides a method of identifying a ligand of a receptor protein, comprising: providing a transfection complex immobilized on a surface, said complex comprising first and second nucleic acids and first and second complexing agents, said first nucleic acid encoding a receptor and said second nucleic acid encoding a protein, wherein said first and second nucleic acid are present in at least one expression vector, and said first complexing agent comprising a ligand for a receptor, said second complexing agent comprising a DNA binding molecule, and a cell; and contacting the cell with said complex under conditions such that cell is co-transfected with the nucleic acids and the nucleic acids are expressed; and detecting the presence of a ligand-receptor binding pair, wherein the receptor protein is encoded by said first nucleic acid.

In a further aspect, the present invention provides a method of identifying DNA binding proteins, comprising: providing a transfection complex immobilized on a surface, said complex comprising a first and a second nucleic acid and at least one complexing agent, wherein the first nucleic acid encodes a protein and is present in an expression vector and wherein the second nucleic acid is not present in an expression vector, and a cell; contacting the cell with the immobilized nucleic acids under conditions such that the cell is co-transfected with the nucleic acids and the nucleic acids are expressed; and detecting the presence of binding between the second nucleic acid and a protein which binds to the second nucleic acid.

In another aspect, the present invention provides a method of analyzing the effect of an analyte, comprising: providing a transfection complex immobilized on a surface, the complex comprising nucleic acid and at least one complexing agent, wherein the nucleic acid encodes a protein, and the nucleic acid is present in an expression vector, and a cell; contacting the cell with the immobilized nucleic acid under conditions such that the cell is transfected with the nucleic acid and the nucleic acid is expressed; adding an analyte to the transfected cells under conditions such that the analyte interacts with a protein encoded by the transfecting nucleic acid; and detecting the effect of the analyte on the protein.

In yet another aspect, the present invention provides a method of identifying a post-translational modified protein, comprising: providing a transfection complex immobilized on a surface, the transfection complex comprising a nucleic acid and at least one complexing agent, wherein the nucleic acid encodes a protein and the nucleic acid is present in an expression vector, and a cell; contacting the cell with the immobilized nucleic acid under conditions such that the cell is transfected with the nucleic acid and the nucleic acid is expressed; and detecting a post-transcriptional modification of the protein.

The present invention also provides a method of immobilizing nucleic acid to a surface, comprising: combining nucleic acid with at least two complexing agents so as to form at least one transfection complex, wherein the complexing agents are selected from the group consisting of polysaccharides, lipids and dendrimers; and contacting the at least one transfection complex to the surface under conditions sufficient to immobilize the nucleic acid. These transfection complex may then be used to transfect a cell by any of the methods as described above; a collection of transfection complexes may also be used to form arrays of transfection complexes, as described above. The invention further provides transfection complexes comprising nucleic acid and complexing agents selected from the group consisting of polysaccharides, lipids and dendrimers; and surfaces comprising such immobilized transfection complexes.

The present invention also provides a method of transfecting a cell, comprising: providing a transfection complex immobilized on a surface, said complex comprising nucleic acid and first and second complexing agents, said first complexing agent comprising a ligand for a receptor, said second complexing agent comprising a DNA binding molecule, and a cell; and contacting the cell with the immobilized transfection on the surface under conditions such that the cell is transfected using an active transport process.

DEFINITIONS

Figure 1:
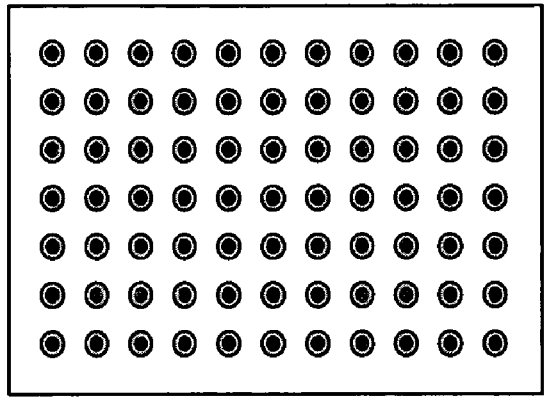
FIG. 1 shows a diagram of STEP. An ordered array of nucleic acids (preferably cDNA clones in eukaryotic expression vectors) is immobilized to a surface, adherent cells are plated onto the nucleic acid array, and following STEP transfection the transfected cells are assayed for effects of expression of the transfected nucleic acid.
Figure 1:
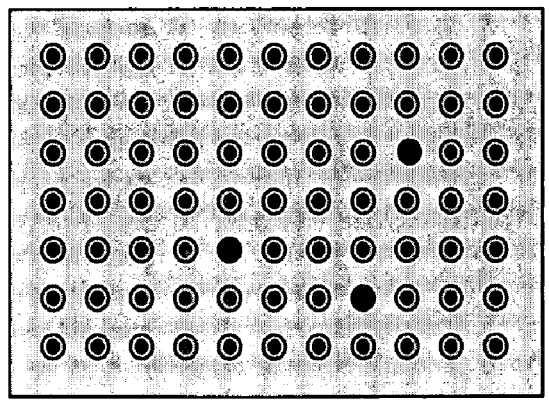

To facilitate an understanding of the present invention, a number of terms and phrases as used herein are defined below:

The term "protein kinase" refers to proteins that catalyze the addition of a phosphate group from a nucleoside triphosphate to an amino acid side chain in a protein. Kinases comprise the largest known enzyme superfamily and vary widely in their target proteins. Kinases may be categorized as protein tyrosine kinases (PTKs), which phosphorylate tyrosine residues, and protein serine/threonine kinases (STKs), which phosphorylate serine and/or threonine residues. Some kinases have dual specificity for both serine/threonine and tyrosine residues. Almost all kinases contain a conserved 250–300 amino acid catalytic domain. This domain can be further divided into 11 subdomains. N-terminal subdomains I–IV fold into a two-lobed structure which binds and orients the ATP donor molecule, and subdomain V spans the two lobes. C-terminal subdomains VI–XI bind the protein substrate and transfer the gamma phosphate from ATP to the hydroxyl group of a serine, threonine, or tyrosine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue required for maximal catalytic activity, and subdomains VI through IX comprise the highly conserved catalytic core. STKs and PTKs also contain distinct sequence motifs in subdomains VI and VIII which may confer hydroxyamino acid specificity. Some STKs and PTKs possess structural characteristics of both families. In addition, kinases may also be classified by additional amino acid sequences, generally between 5 and 100 residues, which either flank or occur within the kinase domain.

Non-transmembrane PTKs form signaling complexes with the cytosolic domains of plasma membrane receptors. Receptors that signal through non-transmembrane PTKs include cytokine, hormone, and antigen-specific lymphocytic receptors. Many PTKs were first identified as oncogene products in cancer cells in which PTK activation was no longer subject to normal cellular controls. In fact, about one third of the known oncogenes encode PTKs. Furthermore, cellular transformation (oncogenesis) is often accompanied by increased tyrosine phosphorylation activity (See, e.g., Carbonneau, H. and Tonks, Annu. Rev. Cell Biol. 8:463–93 (1992)). Regulation of PTK activity may therefore be an important strategy in controlling some types of cancer.

The terms "protein" and "polypeptide" refer to compounds comprising amino acids joined via peptide bonds and are used interchangeably.

As used herein, where "amino acid sequence" is recited herein to refer to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include post-translational modifications of the deduced amino acid sequences, such as amino acid deletions, additions, and modifications such as glycolsylations and addition of lipid moieties.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The term "a polynucleotide having a nucleotide sequence encoding a gene" or "a polynucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, *Adv. Appl. Math.* 2: 482 (1981)) by the homology alignment algorithm of Needleman and Wunsch (Needleman and Wunsch, *J. Mol. Biol.* 48:443 (1970)), by the search for similarity method of Pearson and Lipman (Pearson and Lipman, *Proc. Natl. Acad. Sci. (U.S.)* 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See e.g., Anderson and Young, Quantitative Filter Hybridization, in *Nucleic Acid Hybridization* (1985)). Other references include more sophisticated computations that take structural as well as sequence characteristics into account for the calculation of $T_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)) and 100 μg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q_replicase, MDV-1 RNA is the specific template for the replicase (Kacian et al., Proc. Natl. Acad. Sci. USA, 69:3038 (1972)). Other nucleic acid will not be replicated by this amplification enzyme. Similarly, in the case of T7 RNA polymerase, this amplification enzyme has a stringent specificity for its own promoters (Chamberlin et al., Nature, 228:227 (1970)). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press (1989)).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap, Plant Mol. Biol. 24:119–127 (1994)) promoters. Such promoters have been used successfully to direct the expression of heterologous nucleic acid sequences in transformed plant tissue.

In contrast, a "regulatable" or "inducible" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual,* 2nd ed., Cold Spring Harbor Laboratory Press, New York (1989) pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6–16.7).

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection complex" refers to a molecular aggregate of molecules including nucleic acid that upon entry into cells will result in changes in gene expression. The number of nucleic acid molecules and the type of nucleic acid molecules can be more than one per aggregate. Typically, a transfection complex comprises nucleic acid with one or more complexing agents.

The term "complexing agent" refers to a compound in a transfection complex other than nucleic acid whose effect is under examination; typically, such agents facilitate transfection with nucleic acid. Some classes of complexing agents bind to nucleic acids through electrostatic, hydrophobic, and/or stearic interactions to form a molecular aggregate; other classes bind to other molecules. Examples of such agents include but are not limited to ligands for receptors, DNA-binding molecules, and membrane permeable molecules. Additional complexing agents include but are not limited to targeting molecules, transcription molecules, nucleic acid degradation inhibitors, and cell growth and integrity modulators.

The term "ligand for receptors" refers to a first molecule, the ligand, which is able to bind to a second molecule, such as a protein, sugar, or lipid, which is associated with a cell membrane. When used in reference to STEP, the ligand binds to a receptor which is located in the plasmalemma and which is endocytosed by the cells; preferably, the receptor is a protein. Examples of such ligands include but are not limited to transferrin and low density lipoprotein particles, which bind to LDL receptors, and viral proteins that are known to bind to integrins. Other examples include but are not limited to other proteins, carbohydrates, hormones, small molecules and drugs.

The term "DNA-binding molecules" refers to molecules (e.g. cationic proteins) which complex with nucleic acid to neutralize its charge and to compact its size; these molecules typically bind to nucleic acids through electrostatic, hydrophobic, and/or stearic interactions to form a molecular aggregate. DNA binding molecules include but are not limited to helix-loop-helix proteins (HLH), zinc finger proteins, DNA intercalators such as aromatic molecules, other nucleic acids, heavy metals such as platinum, antibiotics such as chromomycin A(3) and mithramycin (MTR), and DNA-binding peptides such as the DNA-binding peptide mu from adenovirus. Particularly advantageous DNA-binding molecules are cationic proteins.

The term "cationic protein" refers to a protein or polypeptide with an electrostatic charge of greater than zero at pH 7 in aqueous solution; it is in contrast to an "anionic protein" which is a protein or polypeptide with an electrostatic charge of less than zero under the same conditions. In the present invention, a "cationic protein" is a subclass of "DNA binding molecules," which is a subclass of "complexing agents."

The term "membrane permeable molecules" refers to molecules which are permeable in cell membranes, and which facilitate STEP transfection. While it is not necessary to understand the underlying mechanism, and while the invention is not limited to any particular mechanism, it is believed that these molecules facilitate transfection by improving the transport across the membrane of the nucleic acid in a transfection complex into a host cell. Particularly advantageous membrane permeable molecules are cationic lipids.

The term "cationic lipid" refers to a hydrophobic molecule which is lipid soluble and which contains a positively-charged region at pH 7. The present invention contemplates a variety of such cationic lipids, including but not limited to Lipofectamine™, Lipofectin®, Lipofectamine Plus™, Cellfectin®, and Lipofectase™ (available from Life Technologies). In the present invention, a "cationic lipid" is a subclass of "membrane permeable molecules," which is a subclass of "complexing agents."

The term "targeting molecules" refers to molecules which target a transfection complex or portions thereof which contain the nucleic acid to the appropriate cellular compartment in which expression or effect of the nucleic acid occurs; for example, if the nucleic acid is DNA, the appropriate compartment may be the cell nucleus, a mitochondria, or a plastid; if the nucleic acid is RNA, the appropriate compartment may be the cytoplasm, a mitochondria, or a plastid. Such molecules include but are not limited to proteins, for example the SV-40 T antigen, which contain nuclear localization signals (NLSs) to direct the proteins to the nucleus of the cells.

The term "transcription/translation molecules" refers to molecules which promote the transcription of DNA or the translation of RNA. Such molecules include but are not limited to proteins, which include by way of non-limiting example transcription factors, DNA relaxing or unwinding factors (e.g. helicases), and DNA polymerases (e.g. TFIIA, TFIID).

The term "nucleic acid degradation inhibitor" refers to molecules that act as nuclease inhibitors. Such molecules facilitate STEP by preventing degradation of the transfected nucleic acids. Examples of such molecules include but are not limited to proteins (e.g. DMI22) and non-protein drugs.

The term "cell health and integrity modulators" refer to molecules that modulate adherence, growth, proliferation, and/or differentiation of cells; preferably, such modulation promotes these characteristics. These molecules facilitate STEP by modulating, and preferably promoting, the health and integrity of cells transfected with STEP. Examples of such molecules include but are not limited to proteins.

The term "dendrimer" refers to a natural or synthetic branched molecule (e.g. polypeptides, nucleic acids, or synthetic compounds).

The term "type of nucleic acid" refers to a characteristic or property of a nucleic acid that can distinguish it from another nucleic acid, such as a difference in sequence or in physical form, such as occurs in different expression vectors, or as occurs with the presence of DNA and RNA, or as occurs with the presence of linear and super-coiled DNA, or as occurs with the presence of coding regions which encode different proteins, or as occurs with the presence of different control elements, or control elements which differ amongst themselves.

The term "immobilized" when used in reference to nucleic acid refers to a spatial restriction of the nucleic acid on a surface, which restriction prevents the nucleic acid from entering the solution in which the surface is located and becoming free in the solution; it involves stable complex formation, where the complex comprises the nucleic acid and formation of the complex is mediated at least in part by electrostatic interactions. The term "stable" when used in reference to a complex comprising nucleic acid refers to maintenance of the complex for a period of time, generally for at least 72 to 96 hours in a solution, such as tissue or cell culture media. The immobilized transfection complexes are also stable when dried upon a surface; the duration of the stability in the dried state is usually at least several weeks to several months.

The term "array" refers to a pattern, preferably such that the pattern can be replicated and/or detected by an appropriate detector. When used in reference to immobilized transfection complexes of the present invention, an array comprises "spots" containing immobilized transfection complexes. A spot is the location of a single sample of immobilized transfection complexes; a spot may be generated by one or more applications of the sample to the location. Although each spot comprises a single sample of immobilized transfection complexes, a single sample of transfection complexes may comprise from one to more than one type of nucleic acid. Moreover, different spots in an array may comprise the same or different transfection complexes; the transfection complexes may differ in the complexing agents present, the type of nucleic acid present, or both. Typically, different spots differ in the type of nucleic acid present. Thus, an array typically comprises spots at least some to most of which comprise different types of nucleic acids.

A "microarray" refers to an array which is limited to a small area. Typically, such arrays are limited to no more than about 1 inch by 3 inches, as they are frequently generated on microscope slides. Microarrays contain the maximum number of spots which can be created within the limits; typically, this number is less for hand-generated arrays than it is for robotically or machine-generated arrays. A typical machine-generated array contains up to about 10,800 spots.

The term "ordered array" refers to a pattern of spots of the present invention such that the spots are located in a pre-determined geometrical arrangement on the surface; most often, the geometrical arrangement is grid. The term "random array" refers to a pattern of spots of the present invention such that the spots are not located in a pre-determined geometrical arrangement on the surface. A random array can be determined by a mathematical algorithm or by a random number generator.

The term "active transport" refers to a process by which a molecule is transported from outside a cell to inside the cell by any mechanism other than liposomal mediated entry (as for example of DNA coated with lipids), facilitated diffusion, or passive diffusion. Active transport includes endocytosis, particularly receptor-mediated endocytosis. Agents which promote the active transport of nucleic acid molecules inside the cells to aid the transfection process include complexing agents, including but not limited to ligands for receptors, DNA binding molecules, and membrane permeable molecules.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

The term "host cell" refers to any cell capable of replicating and/or transcribing and/or translating a heterologous gene. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 (1987) and U.S. Pat Nos., 6,074, 859; 5,976,796; 5,674,713; and 5,618,682; all of which are incorporated herein by reference), green fluorescent protein (e.g., GenBank Accession Number U43284; a number of GFP variants are commercially available from ClonTech Laboratories, Palo Alto, Calif.), chloramphenicol acetyltransferase, β-galactosidase, alkaline phosphatase, and horse radish peroxidase.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally-occurring source. The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots).

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual*, Cold Spring Harbor Press, NY, pp 9.31–9.58).

The term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39–7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refers to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention. The term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

DETAILED DESCRIPTION OF THE INVENTION

The present invention provides a method of cell transfection, and in particular to the application of cells to nucleic acids which are immobilized on a surface and which then transfect the cells. In one aspect, the method of the present invention comprises the provision of nucleic acids immobilized on a surface; in another aspect, the invention comprises immobilizing nucleic acids on a surface. The nucleic acids are immobilized in a transfection complex comprising the nucleic acid and at least one complexing agent. Preferably, the complexing agents comprise ligands for a cell receptor which is endocytosed by the cell and DNA binding molecules; even more preferably, the transfection complex comprises at least two complexing agents, which are a ligand for a cell receptor which is endocytosed by the cell and a DNA binding molecule. The complexing agents may further comprise membrane permeable molecules which facilitate the passage of DNA complexes across cellular membranes. Additional agents which are optionally present in the transfection complex include targeting molecules that direct the complex or a portion of the complex containing the nucleic acid to an appropriate cell compartment where the nucleic acid can be expressed, transcription molecules that enhance transcription of the DNA, nucleic acid degradation inhibitors, which are molecules that inhibit nucleic acid degradation, and cell health and integrity modulators, which are molecules which modulate and preferably enhance or promote the adherence, growth, proliferation, and/or differentiation of the cells. Thus, in other embodiments, the invention provides transfection complexes, and methods of forming transfection complexes. In yet other embodiments, the nucleic acids are immobilized in an array; preferably, the array is a microarray. In some embodiments, the array is an ordered array; in other embodiments, the array is a random array. In another aspect of the present invention, the method further comprises expression of the nucleic acids in the transfected cells. In yet another aspect of the present invention, the method further comprises detecting the expression of the nucleic acids in the transfected cells. The invention in its different aspects is referred to as Surface Transfection and Expression Procedure (or "STEP"). Additional aspects and details are as follows; in the following description, when the word "DNA" is used, it is used as an example of nucleic acids which may be used in the method of the present invention, and is not meant to be limiting.

The STEP method of the present invention represents an improvement over other forms of transfection. In STEP, nucleic acids are complexed, and the complexes are applied to and immobilized on the surface on which cells are plated or to which cells are exposed. The cells thus contact nucleic acid in an immobilized state. This is in contrast to other methods of transfection, in which nucleic acids are applied to the media in which cells are grown, or are free in the media in which cells are grown. In these other methods, the cells contact nucleic acid which is free in solution. STEP thus allows transfection of cells at the same location where nucleic acid is immobilized. Because the nucleic acids are spatially restricted, with STEP it is possible achieve independent transfections of as many different nucleic acids as can be immobilized on a single surface. Because the nucleic acids are spatially restricted, with STEP it is possible to replicate part or all of any particular array of immobilized nucleic acid, as many times as is desired.

Thus, for example, in one aspect of the present invention, STEP is similar to current uses of DNA microarrays in that with STEP DNA can be applied to a surface (such as a glass slide) utilizing the same robotic devices as are currently used to generate DNA microarrays. Furthermore, for many STEP applications, the same fluorescence slide scanners can be used to quantitate experimental results. However, this is where the similarities end. The DNA applied to the surface, such as a glass slide, is not used in vitro for hybridization, as is the case for current uses of DNA microarrays. Instead, in STEP, the DNA applied to and immobilized on a surface is used to transfect live cells to alter the expression or function of proteins within the cells. It is the actual expression or altered function of the proteins within the cells that is detected. Moreover, the DNA is immobilized as a transfection complex, which complex comprises both nucleic acid and at least one complexing agent; such complexing agents typically facilitate DNA transfection and expression. In some preferred embodiments, at least one complexing agent comprises ligands for a cell receptor which is endocytosed by the cell; in other preferred embodiments, at least a further complexing agent comprises DNA binding proteins; preferably, the transfection complex comprises both ligands for cell receptors and DNA binding molecules.

The method of the present invention has the capacity to functionally screen over 110,000 cDNAs on a single microscope slide (such a slide is typically though not necessarily 25 mm×75 mm). It offers several advantages, including but not limited to that of economy of scale, that for many applications it allows continuous monitoring of function in living cells, that it is easily and completely automated, and that replication is easily accomplished.

Although STEP is very simple, it is believed that the cellular processes of STEP encompass several aspects. Although it is not necessary to understand the mechanism in order to use the present invention, and it is not intended that the invention be so limited, a number of hypotheses are presented to explain the observed results. These hypotheses are presented as beliefs or thoughts. Thus, in STEP, it is believed that the first aspect is cellular adherence to the surface to which nucleic acids are immobilized. Some cationic complexing agents promote the immediate attachment of cells to the immobilized nucleic acid in a transfection complex, while others actually repel the cells. DNA alone, without any complexing agent, repels the cells, as do complexes with low molar ratios of complexing agent to DNA. The second aspect is believed to be cell survival. Some complexing agents appear to show cytotoxic effects, even if cells can adhere immediately. This toxicity is particularly true of certain membrane permeable molecules, such as the lipophilic transfection reagents such as Fugene and Lipofectamine in their pure state. These two particular reagents are commonly used in solution for conventional transfection procedures, and are not reported to be toxic at the concentrations used under these conditions. However, when employed in STEP, these reagents are toxic when used at high concentrations and dried before the cells are applied; they can, however, be used at lower concentrations. The third aspect is believed to be actual transfection of the DNA; the efficiencies of transfection appear to vary with cell type and cationic complexing agent. The fourth aspect is believed to be disintegration of the transfection complex, which may in part be cell mediated. Disintegration outside an adherent transfected cell leads to the generation of false positive cells outside of the immediate vicinity of area where the immobilized nucleic acids (transfection complexes) were added. Many complexes, as for example those formed with histones, are stable for 24–48 hours, and some are stable beyond 96 hours. Optimization of STEP for different cells and nucleic acids is thought to require optimization of each of these hypothetical steps through alterations in the nature of the complexing agents and the nucleic acids, as well as in the proportions and ratios of these components in the transfection complex. Guidelines for such optimization are provided subsequently.

During the discovery and development of STEP, twenty-one different experiments were performed initially to begin characterizing the parameters thought to be important to STEP. Fourteen different cell lines, five different reporter plasmids and twenty-two different cationic complexing agents were employed. The vast majority of experiments were assayed by fluorescence microscopy, although luciferase measurements of transfection efficiency were made in some cases. Parameters which initially appeared to affect transfection efficiency included the manner in which the DNA is prepared, the DNA binding molecules, such as cationic proteins, used to prepare the transfection complex, the cell line used, the duration of exposure of the cells to the transfection complexes, the substrate on which the cells are plated which is also the surface on which the DNA is immobilized (glass, plastic, poly-lysine coated glass or plastic, etc), and the density of the cells when they are plated.

Two important variables which can be optimized through routine experimentation are the cell line to be transfected and the DNA binding molecule (such as cationic DNA binding proteins). High transfection efficiency was observed initially with an expression vector encoding green fluorescent protein (EGFP-C1, Clontech) using second generation COS-1-U3G1 cells. These cells were generated by STEP transfection of parental COS-1-U3 cells with pNEW-NEO, a plasmid encoding the neomycin phosphotransferase gene that confers resistance to G-418. Subsequent selection with G418 yielded three different cell lines, of which COS-1-U3G1 cells possessed the best transfection efficiency that was approximately 10 fold higher than the COS-1-U3 parental cells. It was also found that the source of the cell line is important; several independent lines of COS-1 cells obtained from other sources did not transfect with high efficiency.

Complexing agents are necessary to immobilize the nucleic acids; for example, DNA applied to the surface alone appeared to dissociate from the surface, resulting in very low transfection efficiencies. When cationic proteins alone were complexed to nucleic acids, histones appeared to be the best complexing agent, resulting in an approximately 5 fold increase in transfection efficiencies when compared to poly-L-lysine (70–150 kd) used originally. Using COS-1-U3G1 cells and histones, a 20–30% transfection efficiency was initially obtained, where 100% efficiency indicates that every "spot" of DNA applied has at least one positive cells associated with it. However, these low transfection efficiencies suggested that most of the DNA in the histone:DNA complexes dissociated, resulting in low transfection efficiencies. Increased transfection efficiencies were obtained by the inclusion in the transfection complex of a ligand which binds to a cell receptor which is endocytosed; preferably, the ligand is conjugated to the cationic protein. For example, when 293-HEK cells are utilized, polylysine linked to transferrin resulted in high transfection efficiencies. Further increases in transfection efficiencies were observed with the inclusion of at least one cationic lipid. Optimization of the parameters results in each nucleic acid "spot" having multiple positive cells associated with it.

Immobilized Nucleic Acids

In the present invention, nucleic acids are applied to a surface as transfection complexes; subsequently, the nucleic acid is immobilized within the complex to the surface. Transfection complexes are formed by adding at least one complexing agent to the nucleic acids; preferentially, the complexing agents comprise ligands for a receptor which is endocytosed by the cell to be transfected and DNA binding molecules, such as cationic proteins. In other preferred embodiments, the transfection complex comprises at least two complexing agents, which are a ligand for a cell receptor and a DNA-binding molecule. Additional complexing agents include but are not limited to membrane permeable molecules such as cationic lipids. The transfection complex may comprise additional agents which may modulate or enhance any of a number of additional processes which affect expression of the nucleic acid; such processes include but are not limited to transfer of the nucleic acid to the appropriate cellular location in which to exert its effect, inhibition of degradation of nucleic acid, modulators of transcription or translation, and modulators of cell growth and integrity. The nucleic acids within the transfection complex are immobilized by adhering to the surface to which they are applied.

Although it is not necessary to understand the mechanism in order to use the present invention, and it is not intended that the present invention be so limited, it is useful to think of the nucleic acid as a "scaffold" to which the various complexing agents are added. When present, DNA binding molecules such as cationic proteins of the complex adhere to the nucleic acids, but generally do not interact with the ligands. The ligands are therefore bound in some manner to the DNA alone or to the DNA binding molecules when present; preferably, the ligands are covalently bound to DNA binding molecules, which are preferably cationic proteins. The ligands also preferably bind to receptors on the cell membrane that are endocytosed, to facilitate endocytosis of the nucleic acids. When present, cationic lipids adhere or bind to the nucleic acids and also facilitate the passage of the nucleic acid into the cells. Finally, the cells adhere to the nucleic acids of the transfection complex via the ligand, as well as to the surface to which the nucleic acids are immobilized. Generally, the surface to which the nucleic acids are immobilized is coated. It is believed that the cells adhere to the surface, with or without a coating present, with a lower affinity than they do to the ligand of the transfection complex.

It is also believed that the presence of a ligand for a receptor results in active transport of the nucleic acid into the host cell. By "active transport" in the context of the present invention is meant a process by which a molecule is transported from outside a cell to inside the cell by any mechanism other than liposomal transport, facilitated diffusion or passive diffusion. Active transport includes endocytosis, particularly receptor-mediated endocytosis. Agents that promote the active transport of nucleic acid molecules from outside to inside the cells to aid the transfection process according to the present invention include but are not limited to complexing agents which comprise ligands for receptors, such as proteins, carbohydrates, hormones, small molecules, and drugs, DNA-binding molecules, and membrane permeable molecules.

A. Nucleic Acids

Nucleic acids which may be employed in STEP are any sequences for which transfection into a live cell is desired. Such nucleic acids include, but are not limited to, ESTs, PCR products, genomic DNA, cDNA, RNA, oligonucleotides and antisense constructs; such nucleic acids may be present within expression vectors. The nucleic acids include isolated naturally occurring as well as synthetic nucleic acids and nucleic acids produced by recombinant technology.

Particular useful nucleic acids in the present invention comprise genes; such genes include anything the expression of which can be detected, either directly or indirectly. Exemplary genes include transcription factors, cytoskeleton proteins, hormones, oncogenes, metabolic enzymes, ion channels, and reporter genes. A reporter gene may be any fluorescent protein, any enzyme for which immunocytochemical determination is possible ($\beta$-galactosidase, $\beta$-lactamase, etc.), or any protein or epitope tagged protein for which specific antibodies are available. Gene products can be detected directly, as by the products of an enzyme or by antibody binding, or indirectly, as by linked enzyme assays or by effects which alter cell function. Altered cell function which can be detected include changes in the cell polarity, cell pH, cell morphology, or ability of a cell to bind certain compounds. Detection is most typically by fluorescence or luminescence.

In different embodiments of the present invention, one or more than one type of nucleic acid may be present in a single transfection complex. By "type of nucleic acid" it is meant a characteristic or property of a nucleic acid that can distinguish it from another nucleic acid, such as a difference in sequence or in physical form, such as occurs in different expression vectors, or as occurs with the presence of DNA and RNA, or as occurs with the presence of linear and super-coiled DNA, or as occurs with the presence of coding regions which encode different proteins, or as occurs with the presence of different control elements, or control elements which differ amongst themselves. This allows combinatorial analyses of sets of nucleic acid libraries, as well as analyses involving related processes, such as transactivators of gene expression or steps of a metabolic pathway. In one embodiment, four different expression vectors are present in a single transfection complex; an exemplary embodiment is described in Example 4.

The nucleic acids are generally though not necessarily highly purified for transfection. An acceptable measure of purity is an absorbance ratio of 260 nm/280 nm or greater than or equal to about 1.6, and an absorbance ratio of 260 m to 270 nm of less than or equal to about 1. Either CsCl purification or an ion exchange chromatography procedure (Qiagen) generally results in isolated nucleic acids of sufficient purity. Simple alkaline lysis and phenol extraction of bacterial extracts containing plasmids generally results in nucleic acid preparations of insufficient purity. In alternative embodiments, nucleic acids are products of PCR reactions, which may or may not be purified from the reaction mixture in which the PCR products are formed.

In one embodiment of the invention, supercoiled DNA is utilized, which produces high STEP transfection efficiency and is typically isolated by equilibrium density gradient centrifugation in the presence of 1 mg/ml ethidium bromide. The resolved supercoiled DNA is extracted with water saturated butanol to remove the ethidium bromide and isolated by precipitation with ethanol in the presence of sodium acetate. DNA may also be isolated by ion exchange chromatography using cationic chromatography media and elution with NaCl.

1. Expression Vectors

The nucleic acids may be contained within expression vectors. Thus, for example, a nucleic acid sequence may be included in any one of a variety of expression vectors for expressing a polypeptide, and more than one nucleic acid of interest may be included in one expression vector. Alternatively, parts of one gene or nucleic acid may be included in separate vectors. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host cells.

In some embodiments of the present invention, the constructs comprise a vector, such as a plasmid or viral vector, into which a desired nucleic acid sequence has been inserted, in a forward or reverse orientation. The desired nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: pCDNA3.1, pCMV.5, pZEM3, pSI, pCMV.Neo and pTetOn. Any other plasmid or vector may be used as long as it is replicable and viable in the host cells. In some preferred embodiments of the present invention, the expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, the nucleic acid sequence in the expression vector is operatively linked to an appropriate expression control sequence(s) (promoter) to direct mRNA synthesis. A wide variety of promoters can be used, depending on the cell type which will be used in STEP. Promoters can be constitutive, inducible, or transactivated. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. The following promoters have proved particularly useful in STEP: the human CMV promoter, the Rous Sarcoma Viral LTR promoter, the SV40 late promoter, the human enkephalin promoter, the human chorionic gonadotropin promoter, the mammalian tetracycline inducible promoter (Gossen et al., Science 268:1766–1769, 1995) and several synthetic promoters. Additional promoters include CRE-CAT and ENK72 promoters (Huggenvick et al., *Mol Endocrinol* 5: 921–930 (1991)).

In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the nucleic acid of interest by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Polynucleotides

Any polynucleotide or oligonucleotide may be utilized in STEP; exemplary oligonucleotides include but are not limited to straight oligonucleotides and sugar modified oligonucleotides which have increased intracellular stability. Polyoligonucleotides or oligonucleotides may be complexed in a manner similar to expression vectors, although the exact ratio of nucleic acids to complexing agents should be optimized experimentally for specific length of oligonucleotide and chemical form (phosphorothioate, phosphate, etc. linkages).

3. RNA

RNA may also be complexed in a manner analogous to expression vector DNA for use with cells. In one embodiment, iRNA is utilized to transfect S2 *Drosophila* cells for iRNA inhibition of expression (Clemens et al, Proc. Natl. Acad. Sci. 97(12):6499–6503, 2000). Upon entry into a cell, iRNA results in a reduction of the corresponding host cell protein to about zero; thus, in this embodiment, each of about 20,000 genes could be examined systematically and efficiently with STEP. In yet other embodiments of the present invention, STEP is utilized in combinatorial analyses, in which combinations of different iRNAs can be used to transfect a single cell.

4. PCR Products

Nucleic acids which are products of PCR may also be used directly in STEP. By "directly" it is meant that the nucleic acids need not be purified before being used to prepare a transfection complex. In some embodiments, the reaction mixture in which linear DNA is created by PCR is used directly to prepare transfection complexes, as described in Example 14.

B. Complexing Agents

In the present invention, complexing agents are utilized to perform a number of functions. These include immobilizing the nucleic acids and facilitating DNA endocytosis by the cells; additional functions include targeting the DNA to the appropriate cell compartment in which the nucleic acid can be expressed, promoting expression of the nucleic acid, inhibiting nucleic acid degradation, and promoting host cell growth and integrity. A wide variety of complexing agents have been used in STEP; the following general classes of compounds facilitate STEP transfection.

1. Ligands for Receptors

Ligands for receptors which are endocytosed by the cells of interest facilitate the DNA endocytosis by binding to appropriate cell surface receptors which are endocytosed. For this purpose, transferrin is particularly useful, although other ligands of this class may also be used. Other ligands include but are not limited to low density lipoprotein (LDL) particles, which bind to LDL receptors, and viral proteins that are known to binding to integrins. Integrins are transmembrane proteins which are the main receptors for extracellular matrix proteins. Non-limiting examples of such viral proteins include the penton protein, which is an adenovirus protein, HIV protein GP120, equine rhinitis A virus protein VP1, human adenovirus protein E3, and Epstein-Barr virus protein GP350. An advantage of such viral proteins is that they exhibit less cell specificity than do other ligands, and thus are applicable to a wider variety of host cells.

2. DNA Binding Molecules

DNA-binding molecules (e.g. cationic proteins) complex with nucleic acid to neutralize its charge and to compact its size. DNA binding molecules include but are not limited to helix-loop-helix proteins (HLH), zinc finger proteins, DNA intercalators such as aromatic molecules, other nucleic acids, heavy metals such as platinum, antibiotics such as chromomycin A(3) and mithramycin (MTR), and DNA-binding peptides such as the DNA-binding peptide mu from adenovirus. Cationic proteins include but are not limited to polylysines, histones, transcription factors, polyhistidines, polyarginines, spermines, and spermidines. Preferably, the cationic proteins are polyamines; most preferably, they are polylysines. Spermines and spermidines have not been as effective with HEK-293 cells; it is hypothesized that these compounds may be too short.

3. Membrane Permeable Molecules

The use of membrane permeable molecules (e.g. cationic lipids) facilitates STEP transfection; the type and amounts of membrane permeable molecule present in the complex are preferably optimized for the cell type. Particularly advantageous membrane permeable molecules are cationic lipids. Cationic lipids include but are not limited to Lipofectamine™, Lipofectin®, Lipofectamine Plus™, Cellfectin®, and Lipofectase™ (all from Life Technologies). Typically, these cationic lipids comprise a mixture of selected subsets of about 50 naturally occurring and synthetic cationic lipids, which are formulated in ratios optimized for use with specific cell types. In one embodiment, Lipofectamine™ is particularly useful, and in other embodiments, other similar compounds are effective at lower frequency, under the conditions described, for example, in Example 1.

4. Targeting Molecules

Molecules which target the complex to the cell nucleus or to other sub-cellular locations also facilitate STEP; such locations are appropriate for the expression or effect of the transfecting nucleic acid, such as the nucleus, mitochondria, plastids, or the cytoplasm. Such molecules include but are not limited to proteins, for example the SV-40 T antigen, which contain nuclear localization signals (NLSs) to direct the proteins to the nucleus of the cells. Polylysine contains a similar sequence that may similarly direct the complex to the nucleus 5. Transcription/Translation Molecules Molecules which promote the transcription of DNA or the translation of RNA also facilitate STEP. Such molecules include but are not limited to proteins, which include by way of non-limiting example include transcription factors, DNA relaxing or unwinding factors (e.g. helicases), and DNA polymerases (e.g. TFIIA, TFIID).

6. Nucleic Acid Degradation Inhibitors

Molecules which act as nuclease inhibitors also facilitate STEP by preventing degradation of the transfected nucleic acids. Examples of such molecules include proteins (e.g. DMI22) and non-protein drugs.

7. Cell Health and Integrity Promoters

Molecules which promote adherence, growth, and/or differentiation of cells also facilitate STEP by promoting the health and integrity of cells transfected with STEP. Examples of such molecules include but are not limited to proteins. Proteins that promote adherence of cells grown in culture to the culture surface include but are not limited to polylysine, fibronectin and collagen. Proteins that promote the growth of cells include but are not limited to growth factors and extracellular matrix proteins. Proteins to promote differentiation of cells include but are not limited to nerve growth factor that stimulates differentiation of PC-12 rat pheochromocytoma cells.

One or more of the complexing agents present in the transfection complex may be covalently linked to one or more other complexing agent in order to promote the association of the desired properties of the proteins. For example, transferrin and polylysine may be chemically cross-linked so that the binding to the transferrin receptor and the internalization of transferrin will recruit the polylysine (and the associated nucleic acids) into the same endosomes as transferrin. Alternatively, linkage of the complexing agents may be accomplished by the expression of the two (or more) of the complexing agents as fusion proteins in bacteria or eukaryotic cells.

C. Immobilization

The present invention provides methods of immobilizing nucleic acid to a surface by forming a transfection complex comprising the nucleic acid and at least one complexing agent, and contacting the transfection complex to the surface such that the nucleic acid is immobilized in the transfection complex. Thus, the invention also provides transfection complexes comprising the nucleic acid and at least one complexing agent, and the invention provides surfaces to which nucleic acids are immobilized in such transfection complexes. Transfection complexes are formed by combining nucleic acid with at least one complexing agent, which preferably comprises a ligand. Additional complexing agents which are preferably present within the transfection complex include DNA binding molecules, and membrane permeable molecules; preferably, such agents are cationic proteins and cationic lipids. Alternatively, transfection complex of the present invention comprises at least two complexing agents, which are a ligand and a DNA binding molecule, preferably cationic proteins; additional complexing agents which are preferably present within the transfection complex include membrane permeable molecules, preferably cationic lipids. The ligands is preferentially bound to the DNA binding molecule when present.

In one embodiment of the present invention, nucleic acids are immobilized according to the following steps; these steps are optimized for use with HEK-293 cells expression vectors. It is a matter of routine experimentation to optimize immobilization for use with other cells.

Typically, the nucleic acids, purified or otherwise, are diluted to an appropriate concentration in a solution. Preferred concentrations comprise range from about 0.1 to 10 mg/ml, while most preferably the concentration is 0.12 mg/ml. The solutions include but are not limited to buffers such as Tris and HEPES, and other compounds, at a pH range from about 4 to 9; most preferably the solution is distilled water.

A volume of the diluted nucleic acid is added to a mixture chamber. Appropriate chambers include but are not limited to centrifuge tubes (such as polypropylene), microtiter plates (such as polystyrene), and test tubes (such as glass). Preferably, the chamber is a well of a microtiter plate.

A cationic protein-ligand complex is formed, as in one embodiment by the oxidation of the transferrin, which results in aldehyde formation which then cross-links with the protein. It is important to covalently link the ligand (transferrin) with the cationic protein (polylysine) prior to transfection complex formation; such linkage has been reported for standard transfections in solutions (Wagner et al., Bioconjugate Chemistry 2:226–231, 1991). This complex is then added to the diluted nucleic acids at an appropriate concentration. Preferred concentrations range from about 0.1 to 10 mg/ml, while most preferably the concentration is about 0.4 moles of polylysine as the cationic protein per mole of transferrin with Fe as the ligand. An appropriate volume of the complex added to the nucleic acid; the volume of the complex ranges from about 0.1 to 10 times the nucleic acid volume; preferably, about an equal volume of the complex is added to the nucleic acids. This first nucleic acid mixture is mixed and incubated for an appropriate time at an appropriate temperature. The time ranges from about 30 seconds to about 4 hours, but is preferably about 5 minutes; the temperature ranges from about 0 to 37° C., but is preferably about room temperature (about 18–22° C.).

Alternatively, other cell surface ligands may be used to transfect cells which have low levels of transferrin receptor or when levels of transferrin in the culture media compete with the STEP transfection complexes. A non-limiting example of such proteins is the adenoviral penton protein, which binds to cell surface integrins and which can be used instead of transferrin to transfect many cell types which have less than optimal transfection efficiencies using transferrin in the transfection complex. In these embodiments, the penton protein is used at concentrations of about 0.02 mg/ml to 1.0 mg/ml. When present, the penton protein is preferably bound or linked to a DNA binding molecule; preferably, the DNA binding molecule is a cationic protein; most preferably, the cationic protein is polylysine or histone.

When present, a membrane permeable molecule is then added to the first nucleic acid mixture at an appropriate concentration, forming a second nucleic acid mixture; preferably, the membrane permeable molecule is a cationic lipid. Preferred concentrations of cationic lipids range from about 0.2 to 4 mg/ml; preferably, the concentration is about 1 mg/ml when lipofectamine is the cationic lipid. An appropriate volume of the cationic lipid added to the second mixture, where the volume of the lipid ranges from about 0.1 to 10 volumes of the first nucleic acid mixture; preferably about an equal volume is added to the mixture. This second mixture is then mixed and incubated for an appropriate time at an appropriate temperature. The time ranges from about 30 seconds to 4 hours, but is preferably about 5 min; the temperature ranges from about 0 to 37° C., but is preferably room temperature (about 18–22° C.). This second nucleic acid mixture comprises transfection complexes.

The transfection complex mixture is then applied to a surface. Various surface configurations are contemplated; in the present invention, surfaces include but are not limited to a range from flat to concave to convex to spherical to cubic. The type of configuration depends upon the subsequent application. In one embodiment, the surface is a flat slide. In another embodiment, the surface is a bead. In yet another embodiment, the surface is a cube; in a related embodiment, different transfection complexes are immobilized on different faces or surfaces of the cube, and in yet another related embodiment, different cell types are plated on different faces or surfaces of a cube. In yet another embodiment, the surface is a multiwell tissue culture plate, and the transfection complex is immobilized to the surface of at least one of the wells; in a preferred embodiment, the surface is a 96 well or 384 well tissue culture plate.

Various surface materials are also contemplated; in the present invention, materials include but are not limited to glass, plastic (such as polypropylene, polystyrene), films (such as cellulose acetate) and membranes (such as nylon sheets). The type of material depends upon the subsequent application.

The surface is generally though not necessarily coated with a compound to which both the nucleic acids and cells will adhere. Various coatings are contemplated; in the present invention, coatings include but are not limited to polylysine, fibronectin, and lamenin. The type of coating depends upon both the nucleic acids and the cells. Preferably, for HEK-293 cells and expression vector, the coating is polylysine.

The transfection mixture may be applied by a number of means, including but not limited to direct pipetting, aerosol spraying, electrostatic deposition, and mechanical deposition, as with solid pins. Applications include a single application and multiple applications of a single transfection complex mixture to a single spot. Multiple applications appear to result in multiple layers of transfection complex, and result in increased transfection efficiency. It is believed that the increase in efficiency is due in part to the higher affinity of the cells to the transfection complex, when compared to the affinity of the cells for the surface alone; with multiple layers of transfection complex, it is believed that as one layer of transfection complex is endocytosed, cells bind to the next lower level of transfection complexes, and begin to endocytose these complexes. Preferably, the transfection complex mixture is applied onto a slide using solid pins and multiple applications (2–5 applications). The amount of nucleic acid within a spot depends upon the initial nucleic acid concentration and the volume applied in each application, and the number of applications; preferably, the amount of nucleic is 2 to 500 ng, and most preferably 20–150 ng. The conditions of applying the transfection complex mixture are preferably high humidity; most preferably, the humidity is 70–80%.

The spots of the transfection complex mixture are then dried. Conditions for drying vary and include but are not limited to drying at room temperature (such as in a chamber or in a tissue culture hood), under a vacuum, drying upon application of infrared light, and drying by heating to about from 50 to 200° C. Preferably, the spots dry onto the surface such as a glass slide in a 10 cm tissue culture dish in a tissue culture hood without ultraviolet light.

Typically, more than one sample of transfection complex mixture is applied to a single surface, where each mixture is applied in a spot and each spot comprises only one mixture, which may be singly or multiply applied. The result is an array of spots of immobilized transfection complexes on the surface, where the array is a pattern of spots, preferably such that the pattern can be replicated and/or detected by an appropriate detector. Although each spot generally comprises a single sample of immobilized transfection complexes, a single sample of transfection complexes may comprise from one to more than one type of nucleic acid. Moreover, different spots in an array may comprise the same or different transfection complexes; the transfection complexes may differ in the complexing agents present, the type of nucleic acid present, or both. Typically, different spots differ in the type of nucleic acid present. Thus, an array typically comprises spots at least some to most of which comprise a unique type of nucleic acid per spot. These unique and different types of nucleic acids will then typically have different effects in the cells which are transfected by them; the effects vary, depending upon the use to which STEP is put. The effects of the transfected nucleic acids are then measured by a detector, and the identification of the nucleic acids which have any particular effect is determined by the location of the nucleic acid within the array.

Cells: Types, Preparations, Plating, and Culture

A. Types of Cells

Cells which are applied to immobilized nucleic acids in STEP may be considered host cells. The present invention is directed to both cultured cells and cells freshly obtained from a source (as, for example, freshly dissected out from a tissue or organ). Cultured cells include both primary cultures, cell lines, and three dimensional cultured cells. The present invention is also directed to cells in vivo.

In some embodiments of the present invention, the host cell is a higher eukaryotic cell (e.g., a mammalian cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 (1981)), 293T, C127, 3T3, HeLa and BHK cell lines, NT-1 (tobacco cell culture line), root cell and cultured roots in rhizosecretion (Gleba et al., Proc Natl Acad Sci USA 96: 5973–5977 (1999)). Utilization of plant cells in step may require removal of cell walls, by techniques which are well known in the art.

High transfection efficiencies have been observed with HEK-293T cells, HEK-293 cells, and NIH-3T3 cells. Other cell types such as COS-1 cells may also be used.

B. Cell Culture and Culture Phase

In the present invention, cells are cultured prior to transfection according to methods which are well known in the art, as for example by the preferred methods as defined by the American Tissue Culture Collection or as described (for example, Morton, H. J., In Vitro 9: 468–469 (1974). In one aspect of the invention the cells are then typically treated before they are added to the immobilized transfection complexes; preferably, treatment is trypsinization.

In one embodiment of the present invention, HEK-293T cells are maintained in Delbecco's Modified Eagle's Medium (DMEM) containing 10% fetal calf serum at 37° C. in a humidified tissue culture incubator at 5% $CO_2$. Cells are grown on plastic or glass prior to their use in STEP transfection. When cells reach a confluency of 80% they are passaged by treatment with 0.25% trypsin in 1 mM EDTA to lift the cells off of the growth substrate. Cells are pelleting by centrifugation at 1000×g and the trypsinization media is removed. The cell pellet is resuspended in DMEM and the cells are diluted to approximately four times their original growth volume to give a confluency of 20%. In other embodiments, NIH 3T3 and COS-1 cells are treated in a similar manner.

Cells in the G2/M phase transfect with highest efficiency, so in some embodiments, transfection efficiency is highest with cells that have be synchronized by double-thymidine blockage, aphidocolin treatment or nocodazole treatment as described (Mortimer et al., *Gene Ther* 6: 401–411 (1999); Tseng et al, *Biochim Biophys Acta* 1445: 53–64)).

C. Cell Density

Cell density is an important factor in STEP transfection; in embodiments in which non-three dimensional cell cultures are utilized, initial plating densities of 10 to $10^5$ cells/cm2 are preferred. The higher the cell density, the earlier peak expression will occur, which is thought to be due to contact inhibition at higher densities.

D. Transfected Cells

Cells lines previously transfected using STEP and selected with the appropriate selection agent have shown enhanced transfection efficiencies (approximately 5 to 10 fold). Such cells are preferentially employed in the present invention.

E. Plating

Prepared cells are added to the immobilized nucleic acids by conventional means well known in the art. Typically, in some aspects of the invention which utilize non-three dimensional cell cultures and freshly obtained cells, the cells are present in a media at a particular density; the amount of media and cell density are determined for each cell type and nucleic acid. Preferably, the amount of media added ranges from about 5 to 30 ml/10 cm tissue culture dish; most preferably, about 20 ml of media are added. The cell concentration ranges from about $10^3$ to $10^8/20$ ml plated; preferably $10^6$ cells per 20 ml are added. The number of cells applied to each spot of immobilized transfection complex will depend upon the concentration of cells plated onto the immobilized transfection complexes, the number of spots of immobilized transfection complex, and the density of the immobilized transfection complex spots over which the cells are plated. Preferably, about 1 to 1000 cells are plated per spot of transfection complex; more preferably, about 20 to 100 cells are plated per spot. Preferably, HEK-293 are freshly trypsinized before they are added to the immobilized nucleic acid spots.

The cells are cultured for an appropriate period of time at an appropriate temperature under appropriate atmospheric conditions. The temperature and the atmospheric conditions depend upon the type of cell and the nucleic acids; for HEK-293 cells, the incubation temperature is preferably 37° C. at 5% $CO_2$.

The cells are transfected at an appropriate time during culture; this time depends upon the type of transfection utilized. Typically, the time ranges from about one hour to 30 days, but is preferably about 24 to 72 hours.

In other aspects of the invention that utilize three-dimensional cultured cells, the surface to which nucleic acids are immobilized is applied to the cells. Both the surface and the three dimensional cellular structure are marked so that the array of the immobilized nucleic acids can be correlated with the pattern of detected effects. The cells are transfected under conditions appropriate for such cell culture; preferably, transfection occurs passively.

In yet other aspects of the invention, the surface to which nucleic acids are immobilized are applied to a tissue or organ or other implantable surface in vivo. Such application includes but is not limited to surgical implantation. In some embodiments, the surface is a film or membrane; both the surface and the tissue or organ are marked so that the array of the immobilized nucleic acids can be correlated with the pattern of detected effects. The cells are transfected under conditions appropriate for the specific organ or tissue in vivo; preferably, transfection occurs passively. In one embodiment, the tissue is a tumor, and the detected effect is growth of tumor cells after transfection with the nucleic acids.

Transfection

A. Methods

In some embodiments, various methods are used to enhance transfection of the cells. These methods include but are not limited to osmotic shock, temperature shock, and electroporation, and pressure treatment. In pressure treatment, plated cells are placed in a chamber under a piston, and subjected to increased atmospheric pressures (for example, as described in Mann et al., *Proc Natl Acad Sci USA* 96: 6411–6 (1999)). Electroporation of the cells in situ following plating may be used to increase transfection efficiency. Plate electrodes are available from BTX/Genetronics for this purpose.

In embodiments utilizing 293-HEK cells, the cells are preferably passively transfected by the immobilized nucleic acid complexes.

B. Enhancements

In some embodiments, compounds are included during transfection to increase expression. Such compounds include but are not limited to lysosomal inhibitors such as chloroquine and nuclease inhibitors such as DMI22.

Gene Expression: Detection and Quantitation

In various aspects of the present invention, gene expression is detected by any of several methods, at appropriate times after transfection. The time after transfection depends upon the cells and the nucleic acids; for HEK-293 cells, the cells are cultured undisturbed for at least 16 hours after plating, at which point gene expression can be detected.

A. Fluorescence

Fluorescence of a wide variety of proteins (GFP, DsRed, aqueorin) is measured directly using fluorescence microscopy or microarray slide scanners following appropriate fixation of the slides. Fluorescence microscopy allows continuous monitoring of the same cells over a time course to assay for protein expression, while scanners allow more rapid and accurate quantitation of fluorescence but the cells must be fixed.

Enzyme activities may also be measured using chromogenic or fluorescent substrates in living or fixed cells.

B. Antibodies

Antibodies (M2 Flag as well as others) are also be used to detect the expression of STEP Transfected Proteins.

C. Reporter Assays

Reporter assays generally must be optimized for STEP transfection and optimal conditions may be different from those used in more standard transfection procedure. Important parameters to alter are the amount of reporter vector, the time course of reporter expression, and the proteolytic half-life of the reporter protein used.

D. Selection

Genetic selection is used to isolate stably transfected cells using STEP. Hygromycin, G418 and puromycin selection have all be used with high efficiency. Selection for stable transformants in HEK-293 cells can begin at about 48 hours after plating if desired.

Applications of STEP

The method of the present invention has numerous applications. The following are given by way of illustration, and are not meant to be limiting.

A. Screening Novel cDNA Clones for Function

In one aspect of the present invention, STEP arrays of thousands of expression vectors encoding novel members of the protein kinase family are easily screened for their ability to regulate expression from specific enhancer elements using specific fluorescent reporter constructs. In other aspects of the present invention, novel transcription factors are screened in a similar manner. In yet other aspects of the present invention, the function of many different classes or proteins are assessed using STEP transfection. In one embodiment, a typical analysis of a small family of protein kinases and transcriptional response elements is described in Example 13.

B. Drug Screening

In one aspect of the present invention, STEP arrays of expression vectors for protein tyrosine kinases are treated with various candidate drugs and the in vivo activity of the kinases are determined by fixing and staining the cells with anti-phosphotyrosine antibodies. Since thousands of slide "copies" of the array are easily generated robotically using DNA arrayers, thousands of drugs are screened for in vivo inhibition. Subsets of the kinases are activated by treatment of the STEP transfected cells in culture with various growth factors. In other aspects of the present invention, hundreds of different drug assays employing STEP transfection in a similar manner are contemplated.

In still other aspects of the present invention, STEP is used to analyze the metabolism of drugs. If drugs are identified that alter a pathway that is measured using STEP, then expression vectors for various enzymes that are known to be responsible for drug metabolism, e.g. the cytochrome P450 family, can be included in STEP. If a particular cytochrome P450 was responsible for metabolism of the drug, then co-transfection of the P450 enzyme should attenuate the effect of the drug on the STEP assay. By way of a non-limiting example, the effect of cytochrome P450 on drug PD 1098059, a potent inhibitor of the MAP kinase cascade, is measured. Overexpression of RasV12 activates the Elk-1 reporter in STEP transfected cells, and PD 098059 inhibits this activation. Transfection with various members of the cytochrome P450 family in combination with RasV12 and the Elk-1 reporter reverse the PD098059 inhibition of the Elk-1 reporter if the transfected cytochrome P450 is able to metabolize the PD098059 to an inactive compound.

In further aspects of the present invention, STEP can be used to identify ligands and drugs that act as agonists and antagonists to known or orphan receptors.

C. Mutagenesis Studies

In another aspect of the present invention, STEP arrays are used for screening random mutations of proteins with sufficiently sensitive reporter assays for determining the activity of the mutant proteins. In one embodiment of the present invention, mutagenesis of the autoinhibitory domain of cGMP-dependent protein kinase is investigated, as mutagenesis of this kinase leads to constitutive activation, and a transactivation assay involving the transcriptional regulation of a cyclic AMP-response element-green fluorescent protein (CRE-GFP) reporter construct is utilized to identify constitutively active mutants. In this way, thousands of mutants are screened on a single slide and multiple replicate experiments are easily generated. The collection of mutants are used to define an inhibitory domain within the amino terminus of cGK. In other embodiments of the present invention, many different types of proteins, for which single-cell assays are available or devised for functional readout, are subjected to mutagenesis and analysis in a similar fashion.

In another aspect of the present invention, STEP arrays are used to identify proteins which affect DNA repair. In one embodiment, reporter molecules which contain a single base mismatch at or near the initiation codon (ATG) for GFP reporter construct are generated. The reporter molecule contains the proper base (ATG) in the coding strand of the DNA but a mutant base (CAC in contrast to the normal CAT) in the non-coding strand. Repair of the mismatch on the non-coding strand leads to transcription of mRNAs with the proper RNA sequence to generate a functional GFP molecule. If the DNA repair reporter is co-transfected with a potential DNA repair enzymes using STEP, then the ability of the DNA repair enzyme to repair the DNA mismatch is indicated by cell fluorescence.

D. Antisense Screening

In another aspect of the present invention, STEP arrays containing thousands of antisense oligonucleotides and antisense expression vectors are screened for the ability to inhibit expression of individual proteins. In an embodiment of the present invention, a test system for this application is developed using fluorescent proteins and antisense oligonucleotides as well as antisense constructs as described in Example 12. In other embodiments of the present invention with more widespread applicability, fusion protein constructs between target proteins and fluorescent reporters are used in the screening process. Utilization of the present invention to screen for and identify effective antisense tools has dramatic and positive impacts on the practical use of antisense technology.

E. In vivo Protein Interactions

Fluorescence Resonance Energy Transfer (FRET) has been reported for the in vivo detection of protein interactions and is easily detected in the DNA microarray format using microscopy. A number of in vivo methods have been reported to determine protein-protein association using FRET from genetically encoded variants of the green fluorescent proteins (Zaccolo et al. (2000) Nat Cell Biol 2:25–29; Pollack and Heim (1999) Trends Cell Biol 9:57–60). In yet another aspect of the present invention, libraries of expression vectors for fusion proteins between uncharacterized sequences of interest and a fluorescence donor protein are generated, then in vivo interactions are detected by cotransfection of an expression vector with an appropriate "bait" protein fused to a fluorescence acceptor protein from such a library of fusion proteins.

F. Identification of Protein—Protein Complexes and Post-Translational Modifications.

In yet another aspect of the present invention, STEP is used to identify post-translational modifications of proteins, and to identify protein-protein interactions. In this aspect, a DNA encoding a protein which can be easily purified, preferably in situ, and the mass measured, also preferably in situ, is transfected into cells using STEP. In one embodiment, STEP is performed on a poly-lysine coated cellulose acetate membrane, and at least one transfecting DNA encodes a protein with a hexahistidine epitope tag. The expressed protein is then purified by in situ transfer to a Nickel/NTA affinity membrane; only the hexahistidine tagged protein (and proteins bound to it) binds to the Nickel/NTA affinity membrane, while all the other cellular proteins are washed away. The molecular weight of the purified protein (and any associated proteins) is then determined by MALDI mass spectrometry. Post-translational modifications of the hexahistidine-tagged protein (including but not limited to phosphorylation, glycosylation, proteolytic cleavage) are indicated by an increased molecular weight. In another embodiment, at least a second DNA encoding a second protein is co-transfected with a first DNA encoding a first protein with a hexahistidine tag, and the expressed proteins purified, and the molecular weights determined, as described above. Binding of at least a second protein to the first hexahistidine-tagged protein is also indicated by increased molecular weight.

G. In vivo Cell Transfection

The utility of STEP transfection is widespread, as it is not restricted to transfection of cell lines in culture. In yet another aspect of the present invention, STEP is applied to transfection of primary cultures of cells from a wide variety of tissues and organisms by standard culture methods used for primary cultures. In further aspects of the invention, STEP transfection is used in vivo by implantation of surfaces, such as cellulose acetate membranes, to which transfection complexes have been immobilized. In one set of embodiments, the transfection complexes comprise expression vectors or antisense oligonucleotides; the membranes are implanted into solid tumors in whole organisms, and the effect of STEP transfection on localized tumor cell growth or viability is determined at various periods after implantation.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); Sigma (Sigma Chemical Co., St. Louis, Mo.); CRE (cAMP response element); CREB (cAMP response element binding protein); ATP (adenosine 5' triphosphate); STK (protein serine-threonine kinase); PTK (protein tyrosine kinase); mRNA (messenger RNA); mRNA (heteronuclear RNA); cDNA (complementary DNA); DEAE (diethylaminoethyl); G418 (geneticin); GFP (green fluorescent protein); EGFP (enhanced green fluorescent protein); FRET (fluorescence resonance energy transfer); DMEM (Dulbecco's modified Eagle's Medium); CMV (cytomegalovirus); VASP (vasodilator- and A kinase-stimulated phosphoprotein); PEST (proline, glutamate, serine and threonine rich); Neo (neomycin phosphotransferse); Ca (alpha isoform of the catalytic subunit of cAMP-dependent protein kinase); PKA (cAMP-dependent protein kinase); PKG (cGMP-dependent protein kinase); RRC (ratiometrically responsive cells); SGK (serum- and glucocorticoid-induced protein kinase); PKCa (alpha isoform of protein kinase C); CaMKII (the type II isoform of calcium/calmodulin dependent protein kinase).

EXAMPLES

Example 1

STEP: Surface Transfection and Expression Procedure

In one embodiment, the present invention provides the following method; this method is used in the subsequent examples, unless otherwise noted:
1. Preparation of transfection complexes
  a. Dilute plasmid DNAs to 0.12 mg/ml in $dH_2O$.
  b. Add 1 volume of plasmid DNA to a well of a microtiter plate.
  c. Add 1 volume of transferrin-polylysine complex at 1 mg/ml (0.4 mole polylysine per mole of transferrin with Fe), mix and incubate for 5 min at room temperature.
  d. Add 1 volume of 2 mg/ml lipofectamine, mix and incubate for 20 min at room temperature.
2. Immobilization of nucleic acids
  a. Spot mixture onto slide at high humidity (70–80%) using solid pins and multiple spotting (2–5 spottings).
  b. Allow complexes to dry onto microscope slide in 10 cm tissue culture dish in tissue culture hood without ultraviolet light.
3. Plating and culture of HFK-293 cells
  a. Add 20 ml of media containing 106 freshly trypsinized, exponentially growing HEK-293 cells
  b. incubate at 37° C. at 5% $CO_2$.
  c. Culture cells without disturbing for at least 16 hours after plating.
4. Detection of expression
  Expression of proteins can be detected as early as 16 hours.
5. Selection of transformants (if desired)
  Select for stable transfectants beginning within 48 hours after plating.

Prior to their use in STEP, HEK-293T cells are maintained in Dulbecco's Modified Eagle's Medium (DMEM) containing 10% fetal calf serum at 37° C. in a humidified tissue culture incubator at 5% CO2. The cells are grown on plastic or glass prior to their use in STEP transfection. When cells reach a confluency of 80% they are passaged by treatment with 0.25% trypsin in 1 mM EDTA to lift the cells off of the growth substrate. Cells are pelleting by centrifugation at 1000×g and the trypsinization media is removed. The cell pellet is resuspended in DMEM and the cells are diluted to approximately four times their original growth volume to give a confluency of 20%. NIH 3T3 and COS-1 cells are treated in a similar manner. (Morton, H. J. *In Vitro* 9:468–469, (1974)).

The nucleic acids are preferably supercoiled DNA, which produces the highest STEP transfection efficiency and is typically isolated by equilibrium density gradient centrifugation in the presence of 1 mg/ml ethidium bromide. The resolved supercoiled DNA is extracted with water saturated butanol to remove the ethidium bromide and isolated by precipitation with ethanol in the presence of sodium acetate. DNA may also be isolated by ion exchange chromatography using cationic chromatography media and elution with NaCl.

Example 2

Development of the STEP Transfection Protocol

Green fluorescent protein (GFP) expression vectors (pEGFP-C1, Clontech) and COS-1 or HEK-293 cells were used initially to develop a STEP transfection protocol. Initial attempts to transfect cells in culture with DNA added directly to polylysine coated plates resulted in sporadic, low transfection efficiencies of less than 1 in $10^7$ cells. This was largely due to loss of the DNA from the surface of the plate or slide, as determined by monitoring the fate of fluorescently labeled DNA during the spotting and culture procedures. Complex formation of the DNA with cationic proteins such as poly-lysine or histones resulted in higher transfection efficiencies of 1 in $10^3$ to 1 in $10^4$ however a large number of false positive cells were also observed. These false positive cells were found outside of the areas to which the DNA complex was applied. From careful observation over the time course of transfection, it was determined that the false positive cells resulted from the fragmentation of the DNA complexes and subsequent transfection of cells outside the DNA application area. Chemical cross-linking of the DNA complexes resulted in a decrease in the number of false positive clones, however it also dramatically reduced transfection efficiencies for cells plated on the complex.

The use of cationic lipid/DNA complexes resulted in toxicity to the cells and a lack of expression from cells plated onto the DNA. This toxicity was reduced in a ternary complex of DNA, cationic lipid and histone or poly-lysine. The transfection efficiencies were still low, in the range of 1 in $10^2$ to 1 in $10^3$. However, as previously reported by others, the inclusion of transferrin in the complex and its covalent coupling to the complex resulted in a large increases in solution phase transfection efficiency as determined by reported gene transfection (Zenke, et al., *Proc Natl Acad Sci USA* 87:3655–9 (1990); Cheng, P. W., *Hum Gene Ther* 7:275–82 (1996).

The cell lines shown to be efficiently transfected by the STEP protocol include NIH-3T3 fibroblasts, HEK-293 and HEK-293T cells and with lower efficiency COS-1 and COS-7 cells. Cell lines that have not yet shown efficient transfection include C6 glioma, N1E-115 neuroblastoma, NG-108 neuroblastoma-glioma, C361 and SY5Y cells. Increasing the number of cell lines that are transfected with high efficiency using STEP is described in Example 11. The condition of the cells to be plated and their density are both important to the efficiency of STEP. The cells to be plated are preferably exponentially growing at a confluency of 30–50% prior to trypsinization and are preferably plated at a density of $1–5\times10^4$ cells/cm$^2$ on the applied DNA complexes.

Finally, in this Example, efficient STEP transfection requires that the surface to which the DNA complex is applied be pretreated with poly-lysine and that the DNA complex be applied under conditions of controlled humidity of 70 to 80% and temperature of about 18 to 22° C. If formed properly, the DNA complexes are stable under tissue culture conditions in media for 72 hours or longer.

Using the optimized STEP conditions, transfection efficiencies of 20 to 70% of the cells plated onto the DNA, with very low incidence of false positives (<1%), are routinely achieved. Specific examples are shown below.

Example 3

Detection of STEP Transfected Cells using DsRed Reporter Expression

HEK-293T cells were transfected with an expression vector for DsRed according to STEP in Example 1 and as follows. HEK-293T cells are HEK-293 cells expressing an SV40 T antigen, which allows for high copy replication of expression vectors which contain an SV40 origin of replication. Two hundred nanoliters of a solution consisting of pDsRed-C1 plasmid DNA (Clontech, 20 ng), lipofectamine (130 ng), transferrin (20 ng) and polylysine (40 ng) was applied to the surface of a poly-lysine coated microscope slide. The solution was allowed to dry for 30 minutes and the microscope slide was transferred to a 10 cm tissue culture dish. In this case, HEK-293T cells were plated onto the microscope slide in DMEM containing 10% FCS and the cells were incubated in a humidified 5% CO2 incubator for 48 hours. The expression of DsRed (a red fluorescent protein from marine coral; Fradkov, et al., *FEBS Lett* 479:127–30 (2000)) was determined by fluorescence microscopy. The cells were photographed under brightfield or fluorescence using a rhodamine filter. The outline of the DNA spot can be seen in the brightfield image and the DNA spot itself occupies the lower half of the image. Cell density over the DNA spot is lower than the cell density outside of the spot, in part because cells adhere to the DNA spot less effectively than to polylysine surrounding the spot and in part because cellular replication is inhibited in the transfected cells. In this experiment, transfection efficiency was determined to be 30% and the false positive rate was less than 0.1%.

Example 4

Simultaneous Expression and Detection of More than One Gene

A. Two proteins: GFP and DsReD

Expression vectors for both GFP and DsRed (Fradkov, et al., *FEBS Lett* 479:127–30 (2000)) were used to determine the efficiency of co-expression during STEP transfection according to the procedure in Example 1 and as follows. Transfection complexes were formed from either the two expression vectors separately, or from a mixture of the two expression vectors. Three DNA spots were applied to a standard microscope slide using STEP. The left spot contained only pDsRedC1 expression vector (20 ng), the center spot contained only pEGFPC1 expression vector (20 ng) and the third spot contained an equal mixture of pEGFPC1 and pDsRedC1 vectors (10 ng each). Cells were plated onto the DNA spots and after 24 hours fluorescence photomicrographs were generated using the rhodamine filter set (A) or the fluorescein filter set (B) to detect DsRed or GFP expression, respectively. Both fluorescent proteins were detected in greater than 50% of the cells over the DNA spots and 100% of the DsRed positive cells were also GFP positive. Only 85% of GFP positive cells were also DsRed positive, because of the greater intrinsic fluorescence of GFP protein compared to DsRed protein. Thus, these results show that cells co-express both fluorescent proteins at 100% efficiency, although the sensitivity of detection for EGFP is higher than that for the DsRed expression vector. This high efficiency of co-transfection demonstrates that transactivation assays and other assays that require the interaction of two or more transfected proteins in the same cells can utilize STEP transfection.

B. Four Proteins: EFGP, DsRed, β-galactosidase, and Puromycin Resistance

At least four different expression vectors have been simultaneously introduced into cells using STEP transfection. Transfection complexes were formed from a mixture of all four expression vectors together. Individual cells were simultaneously transfected with EGFP (pEGFP-C1; Clontech), DsRed (pDsRed-C1; Clontech), β-galactosidase (CMV.βgal; Huggenvik et al., Mol Endocrinol 5: 921–930 (1991)) and puromycin resistance (pPUR; Clontech) by STEP; expression of all four proteins was then observed following transfection. Expression of these four proteins was detected by simultaneous green fluorescence, red fluorescence, β-galactosidase cytochemical staining, and growth in the presence of puromycin.

Example 5

Detection of STEP Transfected Cells using Non-Fluorescent Techniques

Although fluorescence is among the most rapid and sensitive of techniques for detection of gene expression, STEP transfected cells can also be detected using a number of different methods. In one method, DNA complexes containing the pTK-Hyg plasmid directing the expression of the hygromycin resistance gene were spotted onto a glass slide and cells were plated onto the slide. Forty-eight hours after plating of cells, hygromycin (100 mg/ml) was added to the media and cells were incubated for an additional ten days with media changes every 3 days. The majority of cells died and were washed away but a photomicrograph showed a "colony" of live cells directly over the STEP transfected spot. Thus, the results showed that transfected cells can be selected using the common selectable markers used for establishing stable transformants including hygromycin resistance, G-418 resistance and puromycin resistance. In another method, the CMV.βgal plasmid (prepared as described in Angelotti et al., Journal of Neuroscience 13: 1418–1428 (1993)) which directs the expression of β-galactosidase was used in STEP transfection. After 48 hours of incubation, the cells were fixed and stained with X-gal (as described in Sanes et al. EMBO J. 5: 3133–3142 (1986)). A photomicrogaph showed both a portion of the spot on the left side of the image and the edge of the DNA spot. The expression of beta-galactosidase was indicated by the dark blue staining of cells within the area of the DNA spot. These results showed that enzymatic detection methods employing cytochemical staining techniques such as beta-galactosidase staining can also be used to demonstrate STEP transfection.

Example 6

Immunocytochemical Detection of Protein Expression using STEP

In order to assay the in vivo function of proteins and to compare the efficacy of effector proteins such as protein kinases in transactivation assays, it will be necessary to demonstrate and quantitate the expression of the effector proteins. One method of doing so involves detecting the proteins immunocytochemically. Such techniques can be effectively utilized in STEP transfection, as is demonstrated by the following experiment.

DNA complexes were formed with either pCMV.Neo empty vector DNA (Vector) or with pFlagVASP DNA (pFlagVASP) which encodes a flag-tagged VASP protein (Collins, et al., *J Biol Chem* 274:8391–404 (1999)), a substrate for phosphorylation by cGMP-dependent protein kinase. For the purposes of this experiment, the pFlagVASP served only as an expression vector directing the expression of a protein carrying the Flag epitope tag. Forty-eight hours after transfection by STEP, the cells were fixed and stained with primary M2 monoclonal antibody followed by a rhodamine conjugated secondary Goat anti-mouse antibody. In a brightfield image of the cells, the DNA spots were clearly visible for both the pFlagVASP and Vector spots. The same set of spots could also be observed in a second image using fluorescence illumination and a rhodamine filter set to detect the rhodamine conjugated secondary antibody. Fluorescence was detected only in cells over spots containing the pFlagVASP expression vector, as was determined by comparing the two images. It was also seen that the expression of the STEP transfected pFlagVASP was highest at the periphery of the spots because these spots were generated at lower than optimal humidity. Thus, the results demonstrated that the expression of a Flag-tagged protein can be specifically detected in cells using STEP transfection, a M2 monoclonal primary antibody and a rhodamine-conjugated secondary antibody. This detection of epitope tagged proteins is used subsequently in Example 8 to establish and quantitate expression of proteins in transactivation assays.

Example 7

Transactivation Assay Using a Tetracycline Inducible System

To determine whether STEP transfection could be modified to generate inducible expression of a protein, the tetracycline inducible system developed by Bujard and coworkers was employed (Baron et al (2000) Proc Natl Acad Sci USA 96:1013–1018). These experiments demonstrate the induction of EGFP expression by doxycycline in HEK TetOn cells following STEP transfection.

Two DNA complexes were prepared for these experiments, one containing the pBi-EGFP plasmid (Clontech) directing the expression of EGFP under the control of a tetracycline responsive element and another complex containing pEGFP-C1 plasmid DNA (Clontech) with EGFP expression under the control of the strong human cytomegalovirus early promoter. Spots for each of these complexes were applied next to each other on each of two different microscope slides and HEK TetOn cells were plated onto each slide in separate 10 cm culture dishes. Twenty-four hours after transfection, one plate was incubated in DMEM and 10% FCS while the other was incubated in the same media containing 10 mg/ml of doxycycline. Fluorescence photomicrographs were prepared 48 hours after plating of the cells. One photomicrograph showed the fluorescence image from the control plate which did not receive doxycycline and two spots were visible; the left spot corresponded to complexes formed with pBiEGFP and the right spot corresponded to the complex formed with pEGFP. In the absence of doxycycline, none of the cells on the pBiEGFP spot were fluorescent while approximately 30% of the cells on the pEGFP-C1 spot were fluorescent. A second photomicrograph showed the fluorescence of cells from the slide treated with doxycycline. Treatment with doxycycline resulted in detectable GFP expression in 20% of the cells on the pBi-EGFP spot which was comparable to the GFP expression seen for the pEGFP-C1 spot on the same slide.

These results showed that expression of GFP could be induced in HEK TetON cells using the tetracycline analog doxycycline. In this experiment, the TetOn transcription factor was stably expressed in all cells plated and the reporter plasmid pBI-EGFP was included specifically in the STEP complex that was applied to the slide. The results showed a clear induction of GFP fluorescence by doxycycline.

Example 8

Transactivation of a Cyclic AMP Responsive Promoter by a Constitutively Active cAMP-Dependent Protein Kinase A transcriptional activation assay (Hall, et al., *J Biol Chem* 274:3485–95 (1999); Taylor, et al., *J Biol Chem* 275:28053–62 (2000)) for measurement of in vivo kinase activity has been adapted and modified for use with STEP transfection. The catalytic (C) subunit of cAMP-dependent protein kinase has been shown by numerous investigators to phosphorylate the cAMP response element binding protein ("CREB") transcription factor and lead to increases in transcription from gene promoters containing the cAMP response element ("CRE") to which CREB binds as a dimer. The canonical CRE nucleotide sequence consists of the palindromic nucleotide sequence TGACGTCA. A reporter plasmid designed to detect increases in CREB activity designated pCRE-d2EGFP (Clontech) has been described (Li, et al., *J Biol Chem* 273:34970–5 (1998)) which contains a CRE enhancer and encodes a destabilized derivative of EGFP (d2EGFP). This destabilized derivative contains a PEST sequence derived from ornithine carboxylase which alters the normal proteolytic half-life of EGFP from 24 hours to 2 hours (Li, et al., *J Biol Chem* 273:34970–5 (1998)). This destabilized EGFP allows for more quantitative measurements of transcriptional regulation without the problems inherent to a long half-life protein.

The pCRE-d2EGFP was used as a reporter plasmid to determine whether co-transfection of the constitutively active catalytic subunit of cAMP-dependent protein kinase would regulate the transcription of pCRE-d2EGFP and result in increased fluorescence compared to control cells which did not receive the C subunit vector. The following experiments describe transcriptional regulation of a CRE-containing expression vector in STEP assays. Transfection complexes were formed with a mixture of pCMV.Neo (2 ng, prepared as described by Huggenvick et al., *Mol Endocrinol* 5: 921–930 (1991)) and pCRE-d2EGFP (18 ng) or pCMV.Ca (2 ng, prepared as described by Huggenvick et al., *Mol Endocrinol* 5: 921–930 (1991)) encoding the C subunit of cAMP-dependent protein kinase and pCRE-d2EGFP (18 ng) and the complexes were applied to the surface of a polylysine coated microscope slide. HEK-293T cells were plated and 24 hours later fluorescence micrographs were obtained using a 4× objective using brightfield illumination, or fluorescence illumination using a fluorescein filter set. Fluorescence images using a 10× objective of a spot containing pCMV.Neo and another containing pCMV.Ca and individual positive cells could be identified. These two fluorescence images were analyzed by pixel density histogram analysis to demonstrate a 16 to 20-fold increase in fluorescent intensity in the STEP transfection with pCMV.Ca compared to that for pCMV.Neo.

These results showed that co-transfection of the constitutively active catalytic subunit of cAMP-dependent protein kinase does indeed regulate the transcription of pCRE-d2EGFP and result in increased fluorescence compared to control cells which did not receive the C subunit vector. Cells plated onto STEP spots containing pCRE-d 2EGFP and empty vector pCMV.Neo show a low average fluorescence. However, cells plates onto STEP spots containing the pCMV.Ca expression vector encoding the C subunit of cAMP-dependent protein kinase as well as pCRE-d2EGFP show a high average fluorescence. The fluorescence from the cells transfected with pCMV.Ca and pCRE-d2EGFP is similar to that seen for the pEGFP-C1, containing the strong constitutive CMV promoter. Detailed examination of the brightfield images shows that there are equal numbers of cells adherent to both DNA spots. Quantitation of the increase in GFP fluorescence using the MicroComputer Imaging Device (MCID) software suggests that cellular fluorescence signal was increased 16 to 20-fold.

Example 9

Use of Fluorescence Slide Scanners for Detection of STEP Transfection

Most of the previous Examples describing aspects of STEP transfection efficiencies have involved fluorescence microscopy. GFP positive cells were not detected because the scanners available did not have the blue Argon excitation laser for optimal GFP detection. However, the DsRed fluorescent protein has excitation and emission maxima of 558 nm and 583 nm which overlaps well with the Cy3 label commonly used for hybridization to DNA arrays for quantitation of gene expression.

The expression of DsRed in STEP transfected cells was detected using an automated scanning fluorescence microarray analyzer as described in the following experiments. DNA complexes were prepared for STEP transfection using the pDsRed-C1 expression vector. Eight DNA spots were observed where the fluorescence intensities for both Cy5 filter sets (ex 649 nm, em 670 nm) and Cy3 filter sets (ex 550 nm, em 570 nm) were shown. The spots are approximately 0.5 to 1 mm in diameter. The DNA complexes spotted differed in their ratios of polylysine, transferrin and Lipofectamine® to the DNA, by weight. These ratios were, for each 120 ng of DNA: 200 to 20 ng polylysine, 800 to 80 ng transferrin, and 2000 to 200 ng Lipofectamine®. Only two DNA spots resulted in efficient STEP transfection of cells; these spots contained the ratios, to 120 ng of DNA: 200, 800, and 2000 ng, and 100, 400, and 1000 ng of polylysine, transferrin, and Lipofectamine®, respectively. The fluorescence signal from these cells was observed only with the Cy3 filter set. A 5× magnification of one of the spots was generated from a TIFF document. Fluorescence photomicrographs of the same spot and a micrograph shows that individual fluorescent cells are discernible. The same fluorescent cells were clearly detected both microscopically and with the slide scanner.

These results demonstrate that STEP transfected cells can be detected using DNA array fluorescence analyzer and fluorescence microscopy. The fluorescence detected from individual cells was specific for the Cy3 filter set and was not seen using the Cy5 filter set. The same cells were detected microscopically using the Rhodamine filter set on a fluorescence microscope. These results demonstrate that quantitation of STEP transfected cells can be adapted to microarray fluorescence analysis for high throughput data analysis of STEP experiments Example 10

Generation of STEP Transfected Cells Using Robotic Arrayers

Figure 2:
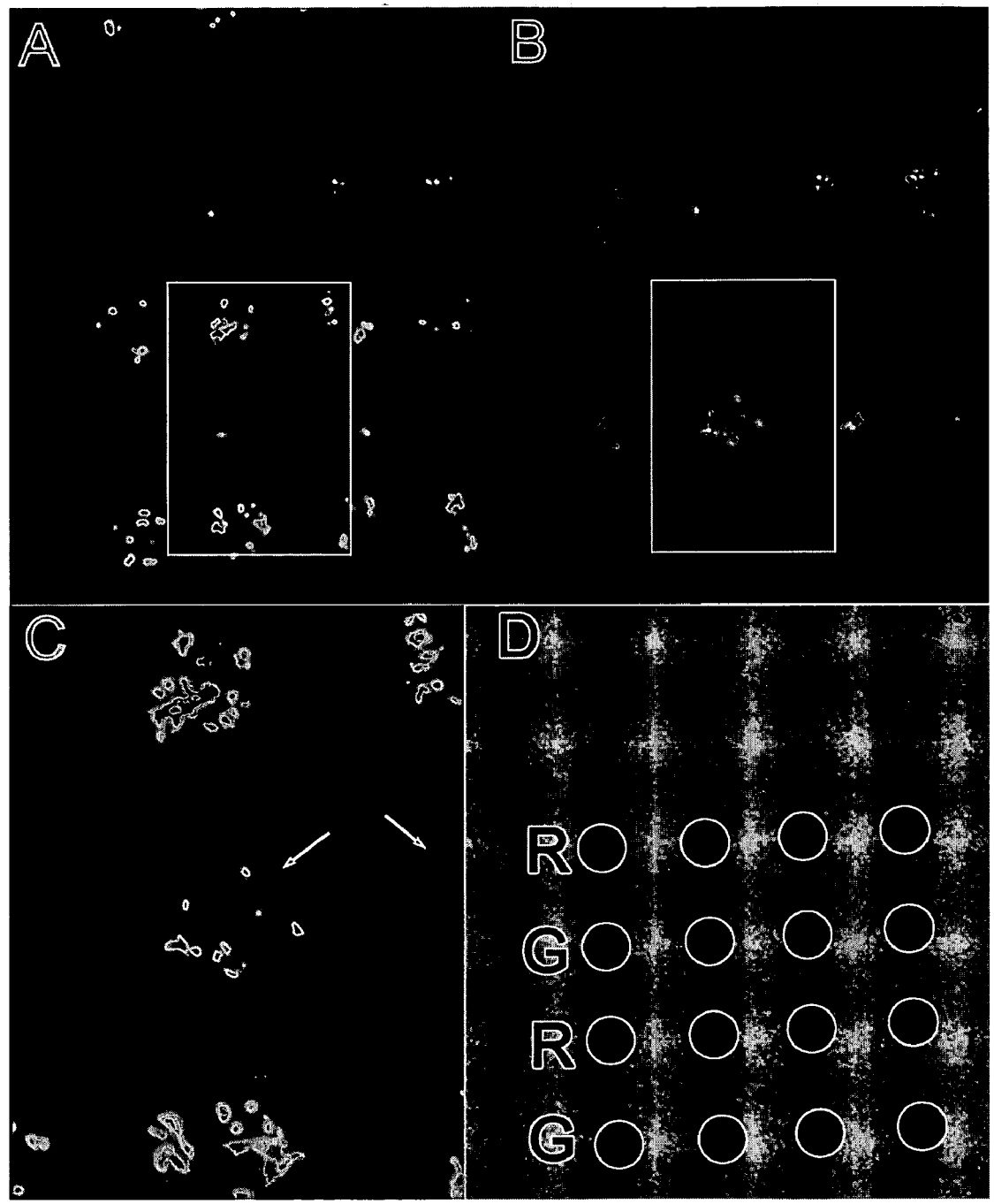
FIG. 2 shows a detection of STEP transfected cells from DNA arrays spotted with a robotic microarray spotter.

DNA complexes have been successfully applied using robotic arrayers to spot the complexes to slides, as described in the following experiment. A 4×4 grid of 16 spots was generated using a robotic spotting station (Genomic Solutions Flexisys). After drying, HEK-293T cells were plated onto the microscope slides and 48 hours later fluorescence micrographs were generated. The results are shown in FIG. 2. In panel(A), the fluorescence of EGFP was detected using a fluorescein filter set at 40× magnification. In panel (B), the fluorescence of DsRed was detected using a rhodamine filter set at 40× magnification. In panel (C), the detection of EGFP and some minimal DsRed "bleed through" fluorescence using a wide bandpass fluorescein filter set at 100× magnification. Arrows indicate the outer circumference of the DNA spots that are just barely visible due to the inclusion of trace amounts of fluorescein in the DNA complex. In panel (D), a schematic shows the type of DNA spots generated with the arrayer the four spots in the first and third rows contained pDsRed-C1 plasmid DNA and the four spots in the second and fourth rows contained pEGFP-C1

The results demonstrate that about 90% of the spots showed at least one positive cell and 50% showed at least 5 or more positive cells. Each spot was in contact with approximately 25 to 30 cells when brightfield images are examined. There are several important parameters in the use of robotic spotters in this experiment. First, the humidity for spotting should be at least 70% or the liquid at the tip of the spotting pin will dry before it can be transferred efficiently to the glass slide. Second, multiple applications of DNA complex to the same spot gives significantly greater transfection efficiency, perhaps due to the formation of laminae of DNA complexes. Third, solid pins are in general more efficient and reproducible than slotted pins in the generation of transfected cells, possibly because the DNA complexes are viscous enough to prevent efficient liquid transfer down the slot

Example 11

STEP Transfection Applied to Mutational Analysis of Protein Function

Optimization of STEP Transfection and Quantitation

STEP transfection can be applied to the study of protein structure and function. Currently, the majority of protein structural studies involve the deletion of predicted domains and the characterization of these deletions on the in vitro and, less often, the in vivo function of the protein. Typically, the role of individual amino acids within a domain of a protein are inferred from homology to other proteins. In this Example, a domain of the cGMP-dependent protein kinase (PKG) is randomly mutagenized and selected for "gain of function" mutants in order to define an inhibitory region of the kinase. STEP allows the functional screening of 1,000 mutants for mutational activation in vivo using a transcriptional activation assay. This Example also outlines the optimization of the STEP method for the application to a multitude of other structure/function studies.

A. Optimization of STEP Transfection and Quantitation

STEP transfection is easily optimized for numerous applications. The experiments in this Example identify important areas that can be optimized. Such optimization of the STEP procedure take advantage of what is currently known about molecular events surrounding transfection. Transfection has generally been thought to consist of three stages (Bally, et al., *Adv Drug Deliv Rev* 38:291–315 (1999)). In the first stage, DNA is taken into the cell by endocytosis. During endocytotic entry the DNA may be either in the fluid phase or adsorbed to the surface of the cell membrane. Inclusion of transferrin in STEP increases the likelihood that the DNA is adsorbed to transferrin receptors on the membrane and will enter endocytic vesicles. The second phase of transfection involves escape of the DNA from the normal lysosomal degradation that occurs with most lysosomal contents. Again, transferrin may help direct the DNA to a subpopulation of endocytic vesicles that are more likely to escape fusion with lysosomes and polylysine may aid in the protection of DNA from lysosomal nuclease. Finally, the last step in transfection is the transport of the DNA to the nucleus where it can be transcribed by RNA polymerases. The efficiency of each of these steps is highly dependent on the form of the DNA complex and the type of cell being transfected.

1. Influence of Cell Cycle on STEP Transfection

It is preferable to have near 100% transfection efficiency for all cells on the DNA complex. The following strategies increase the transfection efficiency further. Initial experiments with STEP have indicated that cells plated for STEP transfection are preferably \in a phase of exponential growth, which is in agreement with other reports (Mortimer, et al., *Gene Ther* 6:401–411 (1999); Tseng, et al., *Biochim Biophys Acta* 1445:53–64 (1999); Brunner, et al, *Gene Ther* 7:401–7 (2000)) that peak transfection efficiencies are obtained with cells in the G2/M phase of the cell cycle. In these studies, transfection efficiency varied as much as 500-fold over the course of the cell cycle. Therefore, HEK-293T cells are enriched in the G2/M phase by different methods. In one method, centrifugal elutriation is used to fractionate cells based on their size and enrich for the larger G2/M phase cells (Brunner, et al., *Gene Ther* 7:401–7 (2000)). Cell fractions are collected and used for plating directly in STEP transfection experiments. In another method, HEK-293T cells are synchronized with a double thymidine block treatment to synchronize cells at G1 phase and then plated onto STEP transfected cells at different times following the removal of the second thymidine block (Tseng, et al., *Biochim Biophys Acta* 1445:53–64 (1999)). In yet another method, use is made of either nocodazole (1 mg/ml), which disrupts G2/M transition by disrupting microtubules, or of aphidicolin (5 mg/ml), which inhibits DNA polymerase and arrests cells in S phase (Mortimer, et al., *Gene Ther* 6:401–411 (1999)). These cell-cycle enriched populations then used in STEP transfection experiments with pEGFP-C1 or pDsRedC1 in a time course used to assay for expression as shown in previous Examples 3 and 4. A 4- to 5-fold increase in transfection efficiency using cells that are enriched in the G2/M phase compared to asynchronously growing cells is preferably observed (Mortimer, et al., *Gene Ther* 6:401–411 (1999)). For HEK and NIH-3T3 cells this means that a 80–90% of the cells are STEP transfected routinely.

2. Treatment During Transfection

It may be preferable to increase transfection efficiencies by treating the cells during the transfection process. Such treatment methods include eletroporation. Electroporation is commonly used as a transfection technique and functions to transiently permeabilize the cell membrane to allow entry of the DNA (Neumann, et al., *Bioelectrochem Bioenerg* 48:3–16 (1999)). In most standard applications, cells are electroporated in cuvettes in the presence of DNA. However, plate electrodes are available for electroporation of cells while they are adherent on surfaces (BTX/Genetronics) and this technique has been used to transfect human umbilical vein cells (HUVECs) with efficiencies comparable to electroporation in a cuvette (Lewis, et al., *Gene Ther* 6:1617–25 (1999)). HEK-293T cells are plated on slides using the standard STEP protocol and then are subjected to electroporation at 1, 4, 12, and 24 hours after plating to determine enhancement of EGFP expression. The electroporation conditions are essentially those defined previously (Lewis, et al., *Gene Ther* 6:1617–25 (1999)), although parameters such as pulse length and voltage around the reported optima are varied (450V and 20 msec). Positive cells are identified by cell counting using fluorescence microscopy and the efficiency of transfection is determined by counting the total cells on brightfield illumination.

Transfection efficiency is also increased by preventing the degradation of DNA in lysosomes. In one method, chloroquine diphosphate, which enters the lysosome and prevents acidification of the lysosomes so that the degradative activity of enzymes is reduced, is used. Chloroquine is added to a final concentration of 100 mM to the medium following cell plating for a period of 0.5 to 4 hours. In another method, the nuclease inhibitor DMI-2, which has been reported previously to increase transfection efficiencies by 10-fold (Ross, et al., *Gene Ther* 5:1244–50 (1998)), is used. DMI-2 is a polyketide metabolite of Streptomyces and its utilization requires purification of DMI-2, the procedure for which is straightforward and takes about three days (Nagao, et al., *J Enzyme Inhib* 10:115–24 (1996)). The purity of the compound is determined by mass spectrometry with an expected molecular weight of 854 Da. A 10-fold enhancement of transfection at DMI-2 concentrations of 250–750 ng/ml is observed, in accordance with results reported by Ross, et al., *Gene Ther* 5:1244–50 (1998).

3. Cell Type

STEP transfection is optimized for application to a great variety of cell lines. Each cell line represents a different milieu for protein expression and comparison of distinct cell types yields maximum amounts of information from STEP experiments.

In quantitation of the efficiency of STEP transfection, efficiency is defined as the percentage of total cells over the applied DNA that are detectably fluorescent. HEK-293T, HEK-293 and NIH-3T3 cells routinely show transfection efficiencies above 30%. COS-1, COS-7 and CV-1 cells have shown transfection efficiencies of approximately 1–5%. Other cell lines tested (C6 glioma, N1E-115, NG-108, C361 and SH-SY5Y neuroblastoma cells) have shown less than 1%. STEP transfection was optimized for HEK-293T cells which showed initial high efficiencies. Generally, optimization involves using two-dimensional arrays of spots in which components of the DNA complex are varied in concentration of type along one of the dimensions of the array. Thus, in a typical experiment, an array of 100 spots is generated that vary the concentration of expression vector DNA and cationic lipid each by a factor of 100, while the concentrations of transferrin and polylysine remain constant. These grids can be been hand-spotted, with each spot approximately 1–2 mm in diameter, so that after plating of the cells we have only 200–400 cells on each spot. With these procedures, it is believed that for many of the lower efficiency cell lines, transfection efficiencies in the range of 0.01 to 1% exist but are not detectable with these procedures. Once transfection efficiencies are detectable, it is possible to optimize transfection by varying parameters such as the time of pre-incubation of various components or by changing the cell density.

Cell lines are screened for high efficiency STEP transfection using minor variation of protocol described in Example 1. These cell lines include but are not limited to those described above, as well as other cell types including CHO, HeLa, MCF-7, A431, BHK and AtT-20 cells. For these assays, larger volumes of DNA complex solution are added so that the area of the DNA spots are 1–2 cm in diameter and 10,000 cells are plated onto each DNA spot. This will allows determination of the transfection efficiency with greater sensitivity in the range of 0.01% to 1%. For HEK-293T cells, the ratio of DNA, cationic protein, cationic lipid and transferrin for complex formation have been optimized. Similar optimizations are carried out for other cell lines. The optimal conditions determined for HEK-293 cells are used as a starting point to screen other cell lines including those observed initially to have lower transfection efficiency (COS-1, COS-7 and CV-1).

4. Genetic Selection of Cells Competent for STEP Transfection

Finally, genetic selection is used to select clonal cells with high STEP transfection efficiencies following STEP transfection. For example, HEK-293T, NIH-3T3, CV-1, and CHO cells are plated onto DNA spots containing the expression vector pTK-Hyg which allows the selection of stably transfected cells in the presence of hygromycin. Stable cells have been selected following STEP transfection and treatment with hygromycin (see previous examples). The process of transfection and selection is believed to enrich for a subpopulation of cells that are more competent for STEP transfection than the parental cell population. Prior to the inclusion of transferrin in the STEP complexes, COS-1 cells were isolated using a G418 selection which transfected with a higher efficiency; however this enhanced efficiency was not maintained as it was rapidly lost between 5 and 10 passages.

A second set of experiments generates cells stably transfected with a constitutive expressed DsRed construct and the pCRE-d2EGFP plasmid. These transfections result in isolation of a cell line with a moderate level of DsRed expression and barely detectable expression of d2EGFP in the basal state. These cells have the potential to provide a much more sensitive measure of induction of the CRE-EGFP reporter, the ratio of fluorescence at the maximum wavelength for EGFP to the fluorescence at the maximum wavelength for DsRed can be used. These cells, referred to as Ratiometrically Responsive Cells (RRCs), normalize for differences in cell morphology that can lead to variation in the intensity of fluorescence observed in STEP transfected cells. The RRCs are used to determine the degree of sensitivity to, or the range of dynamic range of response to secondary transfection with the C subunit of PKA, of a cell stably expressing the CRE-d2EGFP plasmid. The results with RRCs are compared to expression experiments where both the reporter (pCRE-d2EGFP) and the C subunit expression vector are transiently transfected (as described in Example 8). The RRC cell lines are used for quantitation of the fluorescence induction as described below in Section B.

5. Increasing the Efficiency of Detection Beyond GFP

GFP, its mutants with altered spectral properties and other fluorescent proteins have dramatically changed the way that many experiments in gene expression and cellular localization are performed (Tsien, R. Y., *Annu Rev Biochem* 67:509–44 (1998)). However, at the cellular level these fluorescent proteins are relatively inefficient in their detection, since they must attain approximately micromolar levels before they are detectable within cells. Reporter molecules that require cellular disruption, such as luciferase, generally can be detected in vitro at 10 to 100-fold lower levels of expression than those required to detect GFP expression in vivo. It is believed that more cells are transfected during the STEP procedure than we are detectable using fluorescent protein detection. Thus, an alternative reporter system for use in STEP transfection is developed as follows.

Recently, Tsien and coworkers described a novel reporter expression and detection system that employs the *E. coli* b-lactamase enzyme as a reporter (Zlokarnik, et al., *Science* 279:84–8 (1998)). The novel aspect of this system was the mechanism of the enzyme detection, which involved a new substrate molecule for beta-lactamase named CCF2/AM, a cell-permeant acetoxymethyl (AM) ester. Once inside the cell, the AM groups are cleaved by cellular esterases to trap the CCF2 molecule at high concentrations in the cells. CCF2 itself has two fluorescent moieties (a 7-hydroxycoumarin donor fluor and a fluorescein acceptor fluor) that are in close proximity and interact to undergo fluorescence resonance energy transfer (FRET) to generate a green emission (520 nm). However, when CCF-2 is cleaved by beta-lactamase, FRET no longer occurs and the fluorescence emission from the 7-hydroxycoumarin fluor is now in the blue wavelengths (447 nm). The detection of beta-lactamase using CCF2/AM was reported to be 1,000 fold more sensitive than detection of green fluorescent protein on a molecule per cell basis. Furthermore, the beta-lactamase protein has a half-life of approximately 3 hours and allows greater sensitivity to changes in gene transcription than GFP (half-life of 24 hours).

Therefore, cells are STEP transfected with a CMV-beta-lactamase expression vector (Aurora Biosciences), and at 24 or 48 hours later are incubated at room temperature with the CCF2/AM (Aurora Biosciences). Fluorescence determinations employ fluorescence microscopy with excitation at 409 nM, and the ratio of emission at 447 nm (product) is compared with the emission at 520 nm (substrate) to determine the amount of b-lactamase expression. Fixation of the cells with formaldehyde, glutaraldehyde or other reagents may improve quantitative determination of CCF2 fluorescence in fixed cells, so that the CCF2 cleavage can be used in conjunction with DNA microarray slide scanners. Those conditions under which the sensitivity of b-lactamase is shown to be significantly greater than the GFP reporters described in the preceding Examples and in which CCF2 quantitation is adapted to fluorescence scanners are employed when increased sensitivity is desired.

6. Quantitation of Reporter Fluorescence Induction by PKA

The quantitative aspects of the STEP are developed as follows. Image analysis programs have been used to characterize transactivation assays with the C subunit of cAMP-dependent protein kinase and a constitutively active form of the cGMP-dependent protein kinase (PKG) with the Micro-Computer Imaging Device (MCID) and NIH Image imaging analysis applications. Using pixel density histogram analysis from these programs, fluorescence intensities over the STEP DNA spots are increased 16 to 20 fold by inclusion of a constitutively active kinase with the CRE-d2EGFP reporter plasmid. Two different constitutively active kinases have been used for these experiment, either the C subunit of PKA (Gamm, et al., *J Biol Chem* 271:15736–42 (1996)) or the cGKIbS79D mutant of PKG (Collins, et al., *J Biol Chem* 274:8391–404 (1999)). Large amounts of the reporter expression vector (90–95% of the total DNA) may be required for significant induction by the C subunit expression vector (see preceding Examples).

The transcriptional response following STEP transfection are characterized in transfection experiments which include varying amounts of C subunit expression vector (from 0.1% of the total DNA to 5%). The linearity of the response to increasing amounts of C subunit expression vector is determined by quantitating the increase in cellular fluorescence using density histogram analysis. Quantitation of the signal from STEP transfection is significantly different from that for DNA array hybridization experiments, since only a minor fraction of the STEP spot area generates fluorescence signal. In analyses of STEP spots, density histograms are generated for all of the pixels within the two DNA spots to be compared. These histograms are compared and the 2% of pixels with the highest intensity are chosen from each image for quantitation. A roughly linear increase with C subunit expression vector is observed, with perhaps a decline at higher concentrations due to cell morphology changes specifically induced by the C subunit (Huggenvik, et al., *Mol Endocrinol* 5:921–30 (1991); Collins, et al., *J Biol Chem* 274:8391–404 (1999)). The same analysis is also performed with a kinase defective form of the C subunit to ensure that the effect is due to the kinase activity of the C subunit (Brown, et al., *J Biol Chem* 265:13181–13189 (1990)). Once the RRCs are generated as described above, the same analysis is carried out using only the C subunit expression vector and ratiometric imaging using the DsRed fluorescence as an internal standard for expression.

B. The Inhibitory Domain of cGMP-Dependent Protein Kinase is Identified Using STEP Transfection to Screen a Mutational Expression Library These experiments describe the application of STEP to the study of protein structure and function. Currently, a majority of studies employ simple deletion analysis of proteins in order to define functional domains, and then use homology between these domains and known proteins to predict which amino acids within are important to function. STEP transfection and analysis can be used to allow more extensive mutagenic analysis of protein structure and function.

The cGMP-dependent protein kinase (PKG) is selected as an exemplary target for mutagenesis and STEP mediated functional screening. It is a particularly useful target as there is a dearth of knowledge concerning the structure of this protein relative to the cAMP-dependent protein kinases (PKAs). The following paragraphs present a short background to the PKAs and PKGs.

A large number of ligands for seven transmembrane receptors (e.g., epinephrine) alter transcription in their target cells by increasing the intracellular concentration of cAMP. The effects of cAMP are mediated by cAMP-dependent protein kinase (PKA). cAMP binds to the regulatory (R) subunits of PKA causing release of the active catalytic (C) subunit so that it may phosphorylate cellular proteins. A great deal is known about the interactions between the R and C subunits of PKA and how cAMP binding relieves the inhibitory effect of the R subunit (Taylor, et al, *Pharmacol Ther* 82:133–41 (1999)).

Many genes regulated by cAMP contain a palindromic sequence of nucleotides (TGACGTCA) that mediates the transcriptional induction and is known as the cyclic AMP response element (CRE). The CRE binding protein (CRE) binds as a dimer to the CRE and mediates transcriptional regulation only when it is phosphorylated by the C subunit on Ser 133. This pathway has been well established in many cell types (Shaywitz, et al., *Annu Rev Biochem* 68:821–61 (1999).

Atrial natriuretic peptides and nitric oxide do not alter cAMP levels but rather increase in the levels of cGMP in smooth muscle cells and neurons. The majority of cellular effects of cGMP are mediated by the cGMP-dependent protein kinase (PKG) which is similar in structure and function to the cAMP-dependent protein kinase, except that the catalytic component of the kinase is actually fused to the regulatory component as part of the same polypeptide chain. Although much is known about the interactions between the R and C subunits of PKA, little is known about the interactions between the regulatory and catalytic domains of PKG. However, once cGMP binds to PKG it is able to phosphorylate proteins including CREB to mediate changes in gene transcription in a manner analogous to but quantitatively different PKA (Collins, et al., *J Biol Chem* 274: 8391–404 (1999)).

The experiments in this Example delineate the inhibitory region of the regulatory domain of PKG. This information is also useful for the design of specific inhibitors for PKG that do not inhibit PKA. The pCMV.Flag-cGKIb expression vector encoding the Flag-tagged murine cGMP-dependent protein kinase (Collins, et al., *J Biol Chem* 274:8391–404 (1999)) is mutagenized using a combination of sodium nitrite and formic acid treatments as described previously (Orellana, et al., *Proc Natl Acad Sci USA* 89:4726–30 (1992)). Following mutagenesis, the DNA is used as a template for amplification using primers directed against the initiation codon and the codon for Tyr 135, which represents the transition between the amino terminal regulatory domain and the cyclic nucleotide binding domain. The PCR amplified fragments are subcloned into BglII/NheI digest of pCMV.cGKIb and the resulting plasmids are used as a mutational library for screening. Before screening the library, 12 clones are selected at random for sequencing to determine the mutational frequency in the library. From previous characterizations of the mutagenesis procedure, an average of about 2–3 nucleotide substitutions are observed in each mutant clone. Approximately 5–10% of the mutants contain nonsense mutations, and these plasmids do not express functional kinase because translation terminates before the coding region of the catalytic domain. About 80–90% of the clones contain missense mutations. Since perhaps 15 residues make up the autoinhibitory domain, 4–5% of the total number of clones show constitutive kinase activation. A pool of 1,000 clones is screened using STEP transfection, resulting in the observation of about 40–50 individual mutants with constitutive kinase activity. For the clones that demonstrate constitutive activation, the location of the mutations is determined by sequencing the mutagenized region and verifying the constitutive activation of the mutants using standard kinase activity measurements and in vivo luciferase assays.

In the process of screening the mutant library using STEP transfection, the STEP protocol is optimized for high throughput plasmid DNA purification. The 96-well format is used to isolate plasmid DNAs from the mutant clones for transfection, using the QIAwell 96 Ultra Plasmid Kits (Qiagen). Plasmid DNAs are quantitated by UV absorbance and used to generate STEP spots on microscope slides. All 1000 mutant expression vectors along with positive and negative controls for the STEP transfection and EGFP fluorescence quantitation will be spotted. Based on the results of the experiments in Section A, the mutant vectors are either mixed with pCRE-EGFPC1 reporter vector prior to spotting, or the RRCs stably expressing the pCRE-EGFPC1 construct are used (RRCs are described further in Example 11 A 4). The pCMV.Neo parental expression vector and the expression vector encoding the kinase deficient mutant (mCGKIbK404R; Collins, et al., *J Biol Chem* 274: 8391–404 (1999)) are used as negative controls for the screening. The expression vector encoding the constitutively active mutant mCGKIbS79D and the expression vector for the C subunit of cAMP-dependent protein kinase serve as positive controls.

Preliminary results with the mCGKIbS79D in STEP transfections using the pCRE-d2EGFPC 1 result in a 16 to 20-fold induction of EGFP fluorescence with the constitutively active mutants. Other mutations may not produce as great an activation, but several other mutations produce a similar effect.

Example 12

The Use of STEP in Development of Effective Antisense Oligo-Nucleotides

The down regulation of gene expression using antisense strategies has a wide variety of applications from basic research to clinical treatments. This technique has had several notable successes, including the delivery in clinically approved drugs (Nemunaitis, et al., *J Clin Oncol* 17:3586–95 (1999); Yuen, et al., *Clin Cancer Res* 5:3357–63 (1999)). However, it is not widely used because of the difficulty of identifying effective antisense sequences. The mechanism of action of antisense oligonucleotides is unclear in most cases (Crooke, *Biochim Biophys Acta* 1489:31–44 (1999)), although the action of RNase H in degradation of RNA/DNA duplexes has been implicated for many effective antisense oligonucleotides. There is evidence in some cases for additional mechanisms including inhibition of 5' cap formation on mRNAs and translational arrest (Baker, et al., *Biochim Biophys Acta* 1489:3–18 (1999)).

A rapid and efficient means to screen for effective antisense oligonucleotide sequences would have a wide applicability in biomedical research. Such a screening technique would make it possible to develop antisense reagents for any particular gene of interest, allowing the down regulation of protein levels for which no other inhibitory agents are available. STEP transfection has the capacity to allow the screening of thousands of antisense sequences for their efficacy in down regulation of protein levels given the recent advances in oligonucleotide synthesis (Lipshutz, et al., *Nat Genet* 21:20–4 (1999)).

Random sequences of antisense oligonucleotides are screened in STEP format to determine which sequences are capable of interfering with a particular process. For example, antisense oligonucleotides against adenylate cyclase, the catalytic subunit of cAMP-dependent protein kinase, and CREB all have the potential to interfere with the increase in a CRE-EGFP reporter seen in response to isoproterenol acting on the b-adrenergic receptor. Thus, a random library of antisense oligonucleotides is efficiently introduced into cells using STEP transfection, and sequences which interfere with the induction of fluorescence by isoproterenol include sequences complementary to adenylate cyclase, the catalytic subunit of PKA and CREB. As long as a microscopically detectable readout is available for any regulatory pathway of interest, this technique can be used to identify novel components of a signal transduction cascade or any other cellular pathway.

In this Example, STEP transfection techniques are optimized for the entry of oligonucleotides into cells from fixed complexes using a well-characterized control protein and a novel assay for antisense inhibition of expression. Following the optimization of oligonucleotide efficacy using STEP, oligonucleotide sequences are identified which inhibit the production of a target protein kinase for which antisense reagents have not previously been described.

A. Optimization of STEP Transfection for Cellular Delivery of Antisense Oligonucleotides A large number of successful therapeutic applications of antisense have been reported, but the most rigorously tested are those applications that made it to the stage of clinical trials. ISIS3521 is a phosphorothioate antisense oligonucleotide drug based on the sequence of protein kinase C which has had significantly positive effects on the clinical outcome for patients with ovarian and other cancers (Nemunaitis, et al., *J Clin Oncol* 17:3586–95 (1999); Yuen, et al., *Clin Cancer Res* 5:3357–63 (1999)). In this section, an antisense oligonucleotide corresponding to the targeted sequence of human PKCa and a PKCa-EGFP fusion protein is used to identify optimal conditions for STEP mediated inhibition of PKCa protein levels.

An indicator cell line is constructed first. This cell line expresses a PKCa-EGFP fusion protein as well as the DsRed fluorescent protein. A human PKCa-EGFP expression vector is available (Clontech). The reporter cell line is generated by transfecting the pPKCa-EGFP plasmid into HEK-293T cells and selecting for stably expressing clones using G418 resistance and the neomycin phosphotransferase gene contained on the pPKCa-EGFP vector. Several stable cell lines are selected that express high, medium and low levels of the PKCa-EGFP protein; these are then transfected secondarily with a mixture of the pDsRedC1 expression vector and the pTK-Hyg expression vector which encodes resistance to hygromycin (10:1 molar ratio). The pTK-Hyg plas are obtained which differ in the magnitude of expression of both PKCa-EGFP and DsRed. Cell lines that express very high levels of PKCa-EGFP do not show significant reduction in fluorescence but generate the most reproducible results with antisense experiments.

These cell lines are used to determine conditions in which a control antisense PKCa phosphorothioate oligonucleotide (GTTCTCGCTGGTGAGTTTCA (SEQ ID NO:1); ISIS3521), included in STEP complexes, results in a decrease in expression of the PKCa-EGFP fusion protein. The efficacy of the oligonucleotide is first confirmed using standard antisense delivery methods (Dean, et al., J Biol Chem 269:16416–24 (1994)) to treat 60 mm dishes of normal HEK-293T cells followed by western blot analysis of PKCa protein levels. PKCa antibodies are commercially available for this purpose (Upstate Biotechnology, Inc.). Following confirmation of the efficacy of the PKCa antisense oligonucleotide, the same two-dimensional array analysis of the factors that alter transfection efficiency is employed as was utilized for plasmid DNA transfection (see Preliminary Results and Specific Aim 1A). Basically, the type of cationic lipid and protein included in the DNA complex is varied, as is the ratio of the various DNA complex components. Increased pressure enhances the effect of antisense oligonucleotides following STEP, similar to previous reports that pressure treatment increases the uptake of oligodeoxynucleotides (Mann, et al., *Proc Natl Acad Sci USA* 96:6411–6 (1999)). For applying increased pressure, a small Plexiglas chamber with a sealed piston and a pressure gauge is constructed. The chamber is prewarmed to 37° C. and filled with 5% $CO_2$. Each 10 cm tissue culture plate is treated at 1 to 3 atm pressure for 1 to 10 min, and the effect on STEP transfection efficiency is determined as described above.

The conditions for optimal STEP complex formation are generally similar to that for plasmid DNA.

B. Effective Antisense Oligonucleotides for the Serum- and Glucocorticoid Regulated Kinase are Developed Using STEP The procedure for introduction of antisense oligonucleotides into living cells is optimized as described under Section A. The utility of STEP for actually screening antisense oligonucleotides for their ability to down regulate expression is demonstrated by the use of a novel target for antisense down regulation.

Serum- and glucocorticoid-induced protein kinase (SGK) was originally identified in a differential screen to identify mRNAs induced in response to glucocorticoids (Webster, et al., *Mol Cell Biol* 13:2031–40 (1993)). Glucocorticoid or serum stimulation results in a 10-fold elevation of both SGK mRNA and protein. Among the protein kinases, SGK is most homologous to Akt/PKB where it shows 54% amino acid homology over the catalytic domain. Three different isoforms of SGK are expressed widely (Kobayashi, et al., *Biochem J* 344 Pt 1:189–97 (1999)) and all are activated by the phosphoinositide-dependent protein kinase-1 (PDK-1) that is responsive to a multitude of growth factors and cell stimuli. Because many cell stimuli also induce the expression of SGK and the induction is so rapid, SGK has been classified as an immediate early gene. SGK is the only serine/threonine kinase to fall under this classification (Buse, et al., *J Biol Chem* 274:7253–63 (1999)). However, there are no known physiological substrates for this protein kinase and no specific inhibitors of the SGK kinase activity have been reported.

The properties of SGK make it an ideal target for antisense down regulation. First, an effective antisense oligonucleotide would prove very useful in the characterization of downstream effects of SGK and the identification of substrate proteins. Secondly, the short half-life of the protein makes it an ideal target for antisense oligonucleotides because antisense oligonucleotides are most effective against mRNAs encoding proteins with a short proteolytic half-life (Baker, et al., *Biochim Biophys Acta* 1489:3–18 (1999)). Finally, it may be possible to develop antisense oligonucleotides that would discriminate between isoforms of SGK in order to identify isoform-specific functions.

To screen for antisense oligonucleotides, an expression vector encoding a SGK1/EGFP fusion protein is generated in a manner analogous to the PKCa/EGFP expression vector used in Specific Aim 2A. The mouse SGK1 cDNA is obtained either from the laboratory of Dr. Eiten Reuveny at the Weizmann Institute in Rehovot, Israel or by PCR amplification based on the published mouse SGK1 sequence (Genbank accession number AF205855). The half-life of the encoded SGK1/EGFP fusion protein is determined by conventional transient transfection of the vector into HEK-293T cells, then treatment with serum to induce SGK followed by treatment with cycloheximide to inhibit protein translation. Cellular extracts are made at 0, 30, 60, 120 and 240 minutes following cycloheximide treatment and the extracts are analyzed by western blot analysis with antibodies against EGFP. The amount of protein remaining at each time point is determined and a half-life for the protein is calculated. The half-life of the fusion protein is approximately 20–30 minutes, similar to the half-life of SGK. Under some circumstances, EGFP fusion stabilizes the protein. For these circumstances, a second expression vector is generated with SGK fused to the destabilized d2EGFP coding region (Li, et al., *J Biol Chem* 273:34970–5 (1998)), and the half-life of the destabilized construct determined. As described above for the PKCa-EGFP reporter cell line, stable cell lines are generated which express the SGK1-EGFP fusion protein as well as the internal standard DsRed fluorescent protein so that ratiometric imaging can be used to increase the sensitivity of fluorescence scanning.

Originally, 10 different oligonucleotide sequences for the SGK1 mRNA are selected based on their lack of propensity to form hairpin structures and on the predicted stability of the hybrid with the SGK1 mRNA. The length of the oligonucleotides varies from 18 to 24 nucleotides depending on the base composition. Based on our current analysis of the mouse SGK mRNA sequence, the following nucleotide sequences are targeted for the synthesis of the first ten oligonucleotides: 23–43 (21-mer); 38–60 (23-mer); 275–298 (24-mer); 366–389 (24-mer); 826–849 (24-mer); 1252–1270 (19-mer); 1626–1647 (22-mer); 1690–1709 (20-mer); 1859–1880 (22-mer); and 2243–2266 (24-mer). The first two oligonucleotides and the last four oligonucleotides are targeted to the 5' untranslated and 3' untranslated regions which are poorly conserved between the SGK1, SGK2 and SGK3 mRNAs (Kobayashi, et al., *Biochem J* 344 Pt 1:189–97 (1999)). The antisense oligonucleotides possess simple phosphorothioate linkages that have been shown to be effective in many cases.

As described above, the oligonucleotides are complexed with the optimal concentrations of cationic lipid, cationic protein, and transferrin that are found to downregulate the PKCa-EGFP fusion protein as described in Section A. Minor variations of these parameters are optimal for a different oligonucleotide against a different mRNA; therefore, the STEP transfection is optimized for the SGK1 mRNA. Certain conditions are determined such that one of the oligonucleotides above is shown to significantly reduce the fluorescence signal of the SGK1-EGFP (greater than 90% reduction); these conditions are then utilized in the experiments described below to establish the efficacy of the oligonucleotide on down regulation of the native SGK1 mRNA. If conditions which down regulate the SGK1-EGFP reporter with single nucleotides are not easily determined, pools of the oligonucleotides are examined for their effectiveness relative to that of individual nucleotides. A second set of ten additional antisense oligonucleotide sequence are targeted if no combination of the first ten are easily found to be effective. The second set of oligonucleotides will target other regions of the mRNA and will likely include additional modifications to the oligonucleotides such as self-stabilization (Agrawal, S., *Biochim Biophys Acta* 1489:53–68 (1999)).

Once an effective antisense oligonucleotide sequence is defined, the efficacy of the oligonucleotide in the down regulation of the endogenous SGK1 mRNA is determined. For this purpose, NMuMg nontransformed mouse mammary epithelial cells that have recently been developed as a model system for studying the response of SGK1 (Bell, et al., *J Biol Chem* 275:25262–72 (2000)) are utilized. NMuMg cells are plated on control plates or on plates treated to form STEP complexes with the SGK1 antisense oligonucleotides. Following plating, cells are shocked for 3 minutes with 0.3 M sorbitol to induce SGK1 mRNA and protein levels (Bell, et al., *J Biol Chem* 275:25262–72 (2000)). The induction of SGK levels and time course of degradation of the SGK1 protein in the presence of cycloheximide are determined by western blotting using antibody against the SGK1 protein (Upstate Biotechnology). The antisense nucleotide directed against PKCα serves as a negative control for this experiment. The cells plated on the STEP precipitates show a decrease in the induction of SGK1 protein and a decrease in the half-life of the protein following treatment with cycloheximide.

If it is difficult to obtain evidence that the antisense oligonucleotide for SGK1 downregulates the SGK1 protein in NMuMg cells, the NMuMg cells are transfected and stable cell lines expressing the SGK1-EGFP fusion protein are isolated to identify the optimal conditions for antisense treatment with the SGK1 antisense oligonucleotide. NMuMg cells are transfected with moderate efficiency (Bell, et al., *J Biol Chem* 275:25262–72 (2000)). The identification of effective SGK1 antisense oligonucleotides allows their use in further studies characterizing the role of SGK1 in NMuMg cells as well as in other cell lines.

Example 13

Conditions for Functional Screening of cDNA Expression Libraries Using STEP

In this Example, STEP transfection is applied to the functional screening of proteins on a high throughput scale. The exemplary results from protein kinases and the regulation of transcription demonstrate that the high throughput functional screening of proteins using STEP is adaptable to many different areas of research. As another example, STEP is effectively used in a large scale screening of signal transduction pathway components to define functional "modules" important to various aspects of cell metabolism in a manner analogous to that proposed by Hartwell, et al., *Nature* 402:C47–C52 (1999).

A. A Small Library of Constitutively Active Protein Kinases are Screened for their Regulation of cAMP-Response Element (CRE) Dependent Transcription The classical PKA/CREB/CRE mechanism for cAMP regulation of gene expression was established over a decade ago (Gonzalez, et al., *Nature* 337:749–52 (1989)). Since that time, it has been demonstrated that a number of protein kinases are able to regulate gene expression through phosphorylation of CREB or other factors which are able to bind to the CRE. The experiments in this Example determine the ability of a group of 25 different protein kinases to regulate transcriptional activity through the CRE. Constitutively active mutations of all of the protein kinases employed in these experiments are identified and listed in Table 1. These protein kinases were chosen for the diversity of signal transduction pathways that they represent, as well as the extent to which the constitutively active mutations have been characterized in vitro and in vivo.

TABLE 1

Constitutively active kinases and their relevant transcription factors

| Kinase | Transcription | Response | Reference |
| --- | --- | --- | --- |
| PKA | CREB, c-fos, NF-1 | CRE, AP-1, NF-1 | Huggenvik et al., 1991 |
| PKG | CREB | CRE | Collins and Uhler, 1999 |
| PrKX | Unknown | Unknown | Zimmerman et al., 1999 |
| c-raf | Elk-1 | SRE | Leevers et al., 1994 |
| MEKK-1 | p53, c-jun | p53, AP-1 | Fuchs et al., 1998 |
| SEK-1 | c-jun, HSF-1 | SRE, HSF-1 | Guan et al., 1998 |
| MKK-6 | ATF2 | CRE | Raingeaud et al., 1996 |
| MKK-3 | ATF2 | CRE | Raingeaud et al., 1996 |
| ERK-2 | Elk-1, HSF-1 | SRE, HSF-1 | Robinson et al., 1998 |
| PKCα | c-jun | AP-1 | Hansra et al., 1999 |
| PKD (PKCmu) | Unknown | Unknown | Iglesias and Rozengurt, 1999 |
| Akt | CREB | CRE | Kohn et al., 1996 |
| GSK3-β | HSF-1 | HSF-1 | Ohteki et al., 2000 |
| CaMKIIα | CREB | CRE | Komeima et al., 2000 |
| CaMKIV | ATF2 | CRE | Kuno-Murata et al., 2000 |
| ASK-1 | c-jun, Elk-1 | AP-1, SRE | Takeda et al., 2000 |
| TAK-1 | Elk-1 | SRE | Wang et al, 1997 |
| PAK | ATF2 | CRE | Frost et al., 1997 |
| RSK-2 | CREB | CRE | Frodin et al., 2000 |
| ALK-2 | c-myc | E-box | Kawai et al., 2000 |
| IKK-α | NF-κB | NF-κB | Ling et al, 1998 |
| ILK | CREB | CRE | Novak et al., 1998 |
| c-src | CREB, CTF | CRE, CTF | Zang et al., 1997 |

TABLE 1-continued

Constitutively active kinases and their relevant transcription factors

| Kinase | Transcription | Response | Reference |
|---|---|---|---|
| c-Abl | E2F | E2F | Barila et al., 2000 |
| EGFRvIII | Elk-1, c-jun | SRE, AP-1 | Antonyak et al., 1998 |
| Trk-A | Elk-1 | SRE | Gryz and Meakin, 2000 |

In these experiments, each of the constitutively active forms of the kinases is subcloned into an expression vector that provides an amino-terminal or carboxy-terminal Flag epitope tag. This epitope is used to quantitate the amount of protein kinase produced following STEP transfection. The expression vector contains the human CMV promoter directing expression of the kinases, and each of the vectors are tested in normal transfection assays to demonstrate that the appropriate sized protein is synthesized in vivo. The constitutively active expression vectors are prepared according to the references cited in Table 1.

Once confirmed in conventional transient expression experiments, the expression vectors for the constitutively active kinases are used in STEP transfection to determine the efficacy with which they regulate CRE-dependent gene expression. Two different modes of transfection are employed. First, STEP complexes are formed with a mixture of an individual kinase vector with varying amounts of the pCRE-d2EGFP reporter plasmid. These complexes are then spotted and HEK-293T or NIH-3T3 cells plated to determine if co-expression of the kinase results in transcriptional activation of the pCRE-d2EGFP reporter plasmid. Additional cell lines developed as described in Example 11, Section A, are used to investigate the role of cell specific transcription factors in the induction of CRE-dependent transcription. The STEP transfected cells are fixed at various times following plating (6, 12, 24, 48 and 72 hours). A set of triplicate slides are used at each time point for determination of GFP fluorescence (as described in Example 8) and a second set of triplicate slides are used for immunocytochemical staining with the M2 monoclonal antibody to estimate the abundance of the Flag-tagged protein kinase (as described in Example 6). From these two determinations, the relative efficiency of each kinase for stimulation of the CRE-EGFP reporter is determined at each time point. The resulting kinetic profile of transcriptional regulation for each kinase is compared for the 25 different kinases shown in Table 1. Constitutively active forms of PKA, PKG and CaMKII give the strongest induction; some induction is also observed with many of the other kinases (see Table 1), in line with published reports.

In a second series of experiments, the same set of 25 constitutively active kinases are used in STEP transfection with the RRC lines developed as described in Example 11, Section A. The intracellular concentration of CRE sites are much lower in STEP transfections with the RRC lines because the reporter plasmid is not co-transfected with the kinase but is already stably expressed in the reporter cell line. The result is a much more sensitive assay to activation of transcription by constitutively active kinases. In the case of RRC cell lines, varying amounts of expression vectors for the constitutively active kinases are included in the STEP complexes so that increasing amounts of protein kinase are produced. In this way, the minimal amount of kinase required for a transcriptional response is determined by comparing the ratiometric imaging of GFP with the M2 monoclonal antibody staining.

The data obtained is used to generate an induction profile for each kinase over the time course of 72 hours. These profiles are compared on both quantitative and qualitative bases. The result is the identification of novel kinases that may regulate CRE-dependent transcription, as well as the grouping of the kinases into clusters defined by the kinetics of the CRE response. Any differences in such kinetic profiles which are not explained mechanistically in the literature, then serve as motivation investigate that particular kinase pathway in greater detail.

B. The Functional Analysis of the Constitutively Active Protein Kinases Extended to a Larger Set of 21 Different Transcriptional Response Elements Once the response of the CRE to the constitutively active kinases has been determined, the microarray format of STEP transfection is used to determine the response of a set of 21 different characterized transcriptional response elements to the set of 25 constitutively active protein kinases. The response elements employed in these experiments are shown in Table 2.

TABLE 2

Selected Reporter Sequences for Functional Screening of Constitutively Active Protein Kinases

| Reporter/Sequence | Transcription Factor | Reference |
|---|---|---|
| AP-1* (TGACTCA) (SEQ ID NO:2) | c-fos, junB, junD | Fisch et al., 1989 |
| CRE* (TGACGTCA) (SEQ ID NO:3) | CREB, CREM, etc. | Benbrook and Jones, |
| NF-kB*(GGGAATTCC) (SEQ ID NO:4) | NF-kB | 1994 |
| SRE* (60 nucleotides) | Elk-1 | Lernbecher et al., |
| p53* (GAAACTGAAACT) (SEQ (ID NO:5) | p53 | 1993 |

TABLE 2-continued

Selected Reporter Sequences for Functional Screening of Constitutively Active Protein Kinases

| Reporter/Sequence | Transcription Factor | Reference |
|---|---|---|
| ISRE*(AAACTGAAACTG) (SEQ ID NO:6) | Stat1, Stat2, IRF | Treisman, 1990 |
| GAS*(AGTTTCATATTTACTCTAAATC) (SEQ ID NO:7) | Stat1 | Oh et al., 2000 |
| NFAT* (GGAGGAAAAACTGTTCATACAGAAGGCGT) (SEQ ID NO:8) | NF-ATc; NF-ATp | Hiscott et al., 1999 |
| E-box* (CACGTCCACGTC) (SEQ ID NO:9) | | Hiscott et al., 1999 |
| E2F* (CTTGGCGGGAGATAGAA) (SEQ ID NO:10) | c-myc | Northrop et al., 1993 |
| pRb* (60 nucleotides) | E2F-1, E2F-2, E2F-3 | |
| Ets-1 (CCAGGAAG) (SEQ ID NO:11) | pRb | Blackwell et al., 1990 |
| Oct-1 (ATGCAAATGATAT) (SEQ ID NO:12) | Ets-1 | Lam etal., 1995 |
| HNF3(CTAAGTCAATAAT) (SEQ ID NO:13) | Oct-1, Oct-2 | Robbins et al., 1990 |
| C/EBPb (tgcagATTGCGCAATctgca) (SEQ ID NO:14) | HNF3 | Uchijima et al, 1994 |
| CTF (gccAGCCAATgagcgc) (SEQ ID NO:15) | C/EBPb | Kamps et al., 1990 |
| Egr-1 (CGCCCTCGCCCCCGCGCCGGG) (SEQ ID NO:16) | CTF/NF1 | Pani et al., 1992 |
| Delta Factor (CCCCGCTGCCATC) (SEQ ID NO:17) | Egr-1, WT1 | Vinson et al., 1993 Altman etal., 1994 |
| NF-1 (GTTATGGCGACTATCCAGCTTTGTG) (SEQ ID NO:18) | YY-1, F-ACT1, etc | Cao et al., 1990 |
| HSF1 (GAAacCCCtgGAAtaTTcccGAC) (SEQ ID NO:19) | NF-1 | Hariharan et al., 1991 |
| SIE (TTCCCGTAA) (SEQ ID NO:20) | HSF 1 Stat1,2,3 | Hale and Braithwaite, 1995 Abravaya et al., 1991 Boccaccio et al., 1998 |

All of these response elements have been well characterized previously and corresponding reporter vectors have been described. Furthermore, reporter vectors for the majority of these response elements are available commercially (Stratagene and Clontech). Most of the reporter vectors have been designed to employ luciferase as the reporter gene, so that the luciferase coding region is first replaced with the d2-EGFP coding region before they are utilized. Alternatively, the luciferase coding region is first replaced with the b-lactamase reporter system for use in those conditions under which the b-lactamase has substantial advantage over EGFP in terms of sensitivity or quantitation (as described in Example 11, Section A). All of the transfections in these experiments involve co-transfection of the reporter vectors and constitutively active kinases. Alternatively, RRC cell lines are developed for each of the response elements. As described above in Section A, we a time profile for each of the kinase/response element partners is developed in order to characterize the kinetic response of the particular reporter vector.

Over 500 different kinase/response element interactions are tested in a systematic manner. Only 20% of these interactions have been studied previously, so that the majority of these results represent novel information about kinase regulation of gene transcription. Detection of novel positive regulation of transcription for a protein kinase/response element pair is confirmed using standard transfection techniques and a luciferase assay reporter to determine the magnitude of induction.

Several technical questions are addressed by these experiments. First, the various reporters have significantly different basal and stimulated levels of transcription. In this regard, the beta-lactamase expression system is an important alternative to detection because of the greater dynamic range of this reporter system (Zlokarnik, et al., Science 279:84–8 (1998)). Furthermore, the basal expression of the reporter is controlled to some extent by altering the amount of reporter plasmid present in the STEP complexes that are spotted. Those cell lines that have the highest transfection efficiencies in the STEP system are preferably utilized in these experiments. Alternatively, expression vectors for particular transcription factors are included into the STEP complex itself; such transcription factors include but are not limited to CREB, c-jun and fos. These expression vectors are commercially available or prepared as described in the references listed for response elements in Table 2.

Example 14

Use of PCR Products in STEP Transfection

Typically, transient transfection is more efficient using supercoiled DNA than linear DNA. However, bacterial growth and plasmid isolation require a significant time commitment if large numbers of expression vector constructs are to be assayed for protein function. An unexpected advantage of STEP is that it can also be performed with DNA fragments generated by PCR, which need not be purified before use in STEP. This results in significant savings of time, supplies, and effort.

In this Example, primers that flank the CMV promoter and SV40 polyA addition sequence of pEGFP-C1 were used to amplify a 1.8 kb fragment corresponding to the expression cassette for EGFP. Following isolation using a Qiaquik kit (Qiagen), this PCR fragment was used in STEP transfection, resulting in transfection efficiencies of 50%. Similar results have been obtained with expression of the pDsRed-C 1 plasmid. Subsequently, it was determined that it was not necessary to purify the PCR fragment prior to using it to form transfection complexes, such that PCR reaction mixtures can be added directly to complexing agents to form transfection complexes which are then used to form arrays.

Methods:

Oligonucleotides corresponding to sequences 5' of the CMV promoter (ATTACGGGGTCATTAGTTCATA) and 3' of the SV40 poly(A) addition sequence (TCTCGGTCTAT-TCTTTTGATTT) were used to amplify a 1.8 kb fragment corresponding to nucleotides 4721–1770 of pEGFP-C1 using Vent polymerase (New England Biolabs). Following agarose gel electrophoresis, the PCR fragment was isolated using QIAquick purification (Qiagen).

PCR fragments (purified or crude) were diluted to 0.12 mg/ml in water. Ten microliters of plasmid DNA were added to one well of a microtiter plate. Ten microliters of a transferrin-poly-L-lysine complex (1 mg/ml, Sigma) were then added and the mixture incubated for 5 minutes at room temperature. Ten microliters of a 2 mg/ml lipofectamine (Life Technologies, Inc.) were added to this mixture and the resulting solution incubated for 20 min at room temperature. The transfection complex solution was then spotted by hand using a micropipetter to deliver 100 nanoliters. After spotting, slides were allowed to dry for 30 min in a tissue culture hood. The microscope slides were placed into a tissue culture plate (10 cm diameter) and $10^6$ exponentially growing cells in 20 ml of DMEM with 10% FCS were added. The cells were incubated at 37° C. in 5% $CO_2$ following plating.

Results

Using STEP transfection and expression of proteins encoded on linear PCR fragments as described above, approximately 50% of the cells showed EGFP expression.

Example 15

Application of STEP to Assays of Transmembrane Receptor Function

Figure 3:
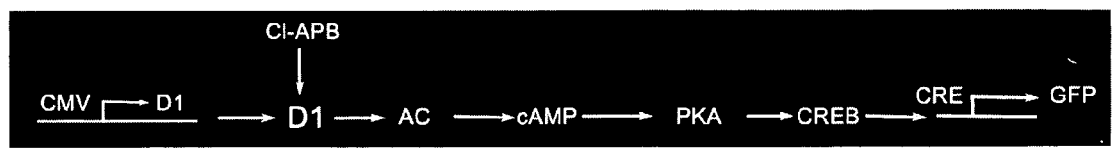
FIG. 3 shows the pathway of the activation of the dopamine 1 (D1) re by C1-APB coupled to adenylate cyclase and subsequent generation of cyclic AMP.

In order to demonstrate the application of STEP to the study of membrane receptor function, the STEP transfection protocol was used to transfect HEK-293T cells with an expression vector for the human D1 dopamine receptor (pCMV.D1) and a cyclic AMP responsive promoter driving the expression of a destabilized green fluorescent protein (pCRE-d2EGFP). The purpose of the experiment was to measure activation of the D1 dopamine receptor by a D1 receptor agonist, Chloro-APB (C1-APB). Activation of the D1 receptor by C1-APB could be measured by virtue of it's coupling to adenylate cyclase and subsequent generation of cyclic AMP, as indicated by the pathway shown in FIG. 3.

Three hundred nanograms of pCMV.D1 (or control vector pCMV.Neo) and 300 ng of pCRE-d2EGFP in 10 microliters were mixed with 10 microliters of transferrin-polylysine complex (1 mg/ml). After 10 minutes, 10 microliters of lipofectamine (1 mg/ml) were added and the mixture incubated for an addition 10 minutes. Spots of approximately 100 nanoliters were placed onto four different polylysine coated microscope slides, and the spots allowed to dry under ambient room conditions. HEK-293T cells were then plated onto three slides, while one slide was grown only in media containing serum. The three slides plated with cells were grown in the presence of either C1-APB or the phosphodiesterase inhibitor IBMX or both C1-APB and IBMX.

After 48 hours, the cells were examined using fluorescence microscopy. The cells expressing the D1 receptor and treated with C1-APB (1 micromolar) showed significantly greater expression of the green fluorescent protein reporter. Quantitation of these results using the MCID image analysis software generated the results shown in Table 3 below.

TABLE 3

Pixels per spot in STEP D1 activation experiment

| DNA/Treatment | Cl-APB + IBMX | Cl-APB | IBMX | Control |
| --- | --- | --- | --- | --- |
| CMV.D1 | 476 + 57 | 447 + 38 | 165 + 35 | 44 + 16 |
| CMV.Neo | 45 + 24 | 46 + 38 | 65 + 32 | 21 + 13 |

Cells transfected with the D1 receptor expression vector and treated with C1-APB showed a ten fold higher level of GFP expression than cells which were transfected with the empty parental vector pCMV.Neo. These results clearly demonstrate that STEP can be used to measure activation of a membrane receptor by a specific ligand and that the activation can be quantitated by determination of GFP fluorescence. The STEP method can be similarly applied to the identification of ligands and drugs that act as agonists or antagonists at other known and orphan receptors.

Example 16

Use of Additional Cell Surface Ligands for Increasing STEP Transfection Efficiency Other cell surface ligands may be used to transfect cells which have low levels of transferrin receptor or when levels of transferrin in the culture media compete with the STEP transfection complexes. One non-limiting example is a protein such as the adenoviral penton protein, which binds to cell surface integrins and which can be used instead of transferrin to transfect many cell types which have less than optimal transfection efficiencies using transferrin in the transfection complex.

For this purpose, the adenoviral penton protein is expressed in either bacteria or in baculovirus-infected Sf9 cells and purified using the methods and techniques as described above. The penton protein may be used at concentrations of about 0.02 mg/ml to 1.0 mg/ml. The purified protein is mixed with the nucleic acid to be transfected along with polylysine or histones and a cationic lipid such as lipofectamine or lipofectamine 2000. After spotting of the complex, cell lines (such as rat PC-12 pheochromocytoma, NG-108 neuroblastoma-glioma hybrid cells, and SH-SY5Y neuroblastoma cells), which normally show low transfection efficiencies (less than 10%) using transferrin, are transfected with efficiencies of 50 to 80% if the adenoviral penton protein is used. Transfection efficiencies may be increased even further by producing fusion proteins containing the penton protein at the amino terminus and DNA binding proteins such as histones at the carboxy terminus.

In the following experiments, transfection complexes were formed as described in Example 1, except that in the preparation of some transfection complexes, purified penton protein was used instead of transferrin; the penton protein was used at a concentration of 0.64 mg/ml. Transfection complexes were thus prepared with either transferrin or penton protein. After immobilizing the complexes as described in Example 1, the cell lines rat PC-12 pheochromocytoma and HEK-293T were transfected as described in Example 1. The transfected cells were then examined by microscopy under brightfield, which shows all the cells, and under fluorescence, which shows just those cells which are expressing GFP.

Figure 4:
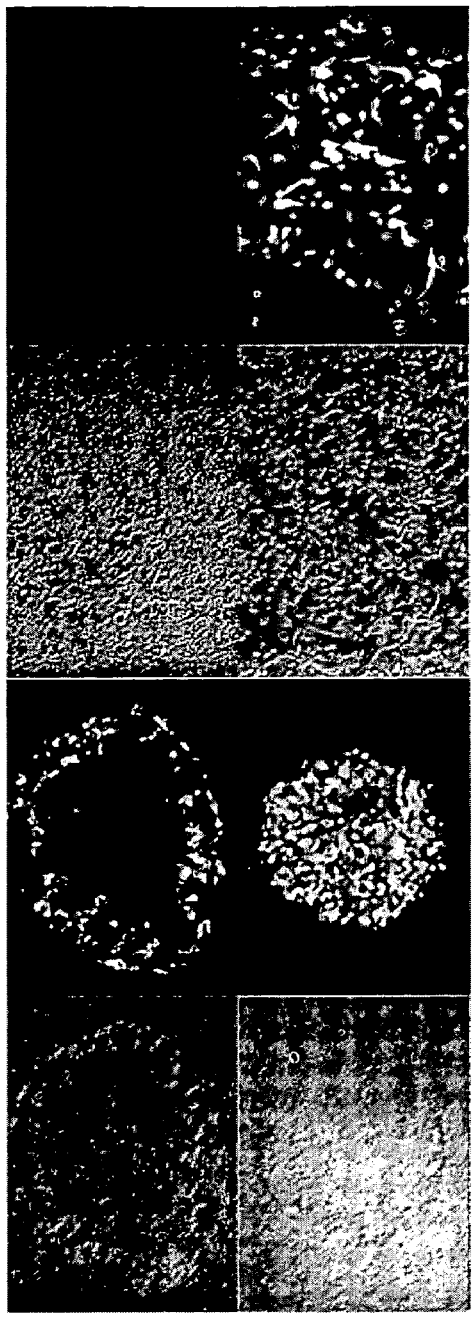
FIG. 4 shows the transfection of two cell types where the adenoviral protein penton is used as a complexing agent in the transfection complexes.

The results are shown in FIG. 4 as sets of images; the cell line is indicated at the top of the images, and the ligand used in the transfection complex is indicated to the right of the images. The images under each indicated cell line are either brightfield images (to the left) or fluorescence images (to the right). These results demonstrate that PC-12 was transfected at low efficiencies using transferrin (less than 10%), and that an increase in transfection efficiency (of 50% to 80%) was observed when the ligand was adenoviral penton protein.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The following printed publications are referred to in the body of the specification:

Abravaya et al. (1991) Mol Cell Biol 11:586–592;
Agrawal, S. (1999) Biochim Biophys Acta 1489:53–68;
Altman et al. (1994) Proc Natl Acad Sci USA 91:3901–3905;
Amundson S A et al. (1999) Oncogene 18(24):3666–72;
Anderson and Young (1985) Quantitative Filter Hybridization, in *Nucleic Acid Hybridization;*
Angelotti et al. (1993) Journal of Neuroscience 13: 1418–1428;
Antonyak et al. (1998) J Biol Chem 273:2817–2822;
Baker et al. (1999) Biochim Biophys Acta 1489:3–18;
Bally et al. (1999) Adv Drug Deliv Rev 38:291–315;
Barila et al. (2000) Embo J 19:273–281;
Baron et al. (2000) Proc Natl Acad Sci USA 96:1013–1018;
Bell et al. (2000) J Biol Chem 275:25262–25272;
Benbrook and Jones (1994) Nucleic Acids Res 22:1463–1469;
Bittner M et al. (1999) Nat Genet. 22(3):213–5;
Blackwell et al. (1990) Science 250:1149–1151;
Boccaccio et al. (1998) Nature 391:285–288;
Brown et al. (1990) J Biol Chem 265:13181–13189;
Brown and Botstein (1999) Nat Genet 21:33–37;
Brunner et al. (2000) Gene Ther 7:401–407;
Buse et al. (1999) J Biol Chem 274:7253–7263;
Cao et al. (1990) Mol Cell Biol 10: 1931–1939;
Carbonneau H. and Tonks (1992) Annu. Rev. Cell Biol. 8:463–493
Chamberlin et al. (1970) Nature, 228:227;
Cheng P. W. (1996) Hum Gene Ther 7:275–82;
Clemens et al. (2000) Proc. Natl. Acad. Sci. 97(12):6499–6503;
Collins and Uhler (1999) J Biol Chem 274:8391–8404;
Collins et al. (1999) J Biol Chem 274:8391–404;
Crooke (1999) Biochim Biophys Acta 1489:31–44;
Dean, et al (1994) J Biol Chem 269:16416–16424;
deWet et al (1987) Mol. Cell. Biol. 7:725;
Duggan et al. (1999) Nat Genet 21:10–14;
Erlich, H. A. (ed.) (1989) *PCR Technology* (Stockton Press);
Fisch et al. (1989). Mol Cell Biol 9:1327–1331;
Fradkov et al. (2000) FEBS Lett 479:127–130;
Frodin et al (2000) EMBO J. 19(12):2924–34;
Frost et al. (1997) Embo J 16:6426–6438;
Fuchs et al. (1998). Proc Natl Acad Sci USA 95:10541–10546;
Gamm, et al. (1996) J Biol Chem 271:15736–15742;
Garbarino and Belknap (1994) Plant Mol. Biol. 24:119–127;
Gill and Sanseau (2000) Biotechnol Annu Rev 5:25–44;
Gleba et al. (1999) Proc Natl Acad Sci USA 96: 5973–5977;
Gluzman (1981) Cell 23:175;
Gonzalez, et al (1989) Nature 337:749–752;
Gossen et al. (1995) Science 268:1766–1769;
Graham and van der Eb (1973) Virol., 52:456;
Graves DJ (1999) Trends Biotechnol. 17(3):127–34;
Gryz and Meakin (2000) Oncogene 19:417–430;
Guan et al. (1998) J Biol Chem 273:28670–28676;
Hale and Braithwaite (1995) Nucleic Acids Res 23:663–669;
Hall, et al. (1999) J Biol Chem 274:3485–95 (1999);
Hansra et al. (1999) Biochem J 342:337–344;
Hariharan et al. (1991) Proc Natl Acad Sci USA 88:9799–9803;
Hartwell, et al. (1999) Nature 402:C47–C52;
Hiscott et al. (1999) J Interferon Cytokine Res 19:1–13;
Huang F et al. (1999) Oncogene 18(23):3546–52;
Huggenvick et al. (1991) Mol Endocrinol 5: 921–93;
Iglesias and Rozengurt (1999) FEBS Lett 454:53–56;
Iyer et al.(1999) Science 283:83–7;
Kacian et al. (1972) Proc. Natl. Acad. Sci. USA, 69:3038;
Kamps et al. (1990). Cell 60:547–555;
Kawai et al. (2000) Biochem Biophys Res Commun 271: 682–687;
Kobayashi, et al. (1999) Biochem J 344 Pt 1:189–197;
Kohn et al. (1996) J Biol Chem 271:31372–31378;
Komeima et al. (2000) J Biol Chem 275:28139–28143;
Kuno-Murata et al. (2000) Endocrinology 141:2275–2278;
Lam et al. (1995) Gene 160:277–281;
Leevers et al. (1994) Nature 369:411–414;
Lembecher et al. (1993) Nature 365:767–670;
Lewis et al. (1999) Gene Ther 6:1617–1625;
Li et al. (1998) J Biol Chem 273:34970–34975;
Ling et al (1998). Proc Natl Acad Sci USA 95:3792–3797;
Lipshutz, et al. (1999) Nat Genet 21:20–24;
Maniatis, et al. (1987) Science 236:1237;
Mann et al. (1999) Proc Natl Acad Sci USA 96: 6411–6416;
Mortimer et al. (1999) Gene Ther 6: 401–411;
Morton, H. J. (1974) In Vitro 9: 468–469;
Nagao et al. (1996) J Enzyme Inhib 10:115–124;
Neumann et al. (1999) Bioelectrochem Bioenerg 48:3–16;
Nemunaitis et al. (1999) J Clin Oncol 17:3586–95 (1999);
Northrop et al. (1993) J Biol Chem 268:2917–2923;
Novak et al. (1998) Proc Natl Acad Sci USA 95:4374–4379;
Oh et al. (2000) Mol Cells 10:275–280;
Ohteki et al. (2000) J Exp Med 192:99–104;
Orellana et al. (1992) Proc Natl Acad Sci USA 89:4726–4730;
Pani et al. (1992) Mol Cell Biol 12:552–562;
Pearson and Lipman (1988) Proc. Natl. Acad. Sci. (U.S.A.) 85:2444;
Pollack and Heim (1999) Trends Cell Biol 9:57–60;

Raingeaud et al. (1996) Mol Cell Biol 16:1247–1255;
Robbins et al. (1990)]. Nature 346:668–761;
Robinson et al. (1998) Curr Biol 8:1141–1150;
Ross et al. (1998) Gene Ther 5:1244–50;
Sambrook et al (1989) *Molecular Cloning: A Laboratory Manual, 2nd ed.* (Cold Spring Harbor Laboratory Press, New York) pp. 16.7–16.8;
Sanes et al. (1986) EMBO J. 5: 3133–3142;
Schena et al. (1995) Science 270: 467–470;
Shaywitz, et al. (1999) Annu Rev Biochem 68:821–861;
Smith and Waterman (1981) Adv. Appl. Math. 2: 482;
Takeda et al (2000). J Biol Chem 275:9805–9813;
Taylor, et al. (1999) Pharmacol Ther 82:133–141;
Taylor, et al. (2000) J Biol Chem 275:28053–28062;
Treisman (1990) Semin Cancer Biol 1:47–58;
Tseng et al. (1999) Biochim Biophys Acta 1445: 53–64
Tsien R. Y. (1998) Annu Rev Biochem 67:509–544;
Uchijima et al (1994) J Biol Chem 269:14946–14950;
Vinson et al. (1993) Genes Dev 7:1047–1058;
Voss et al. (1986) Trends Biochem. Sci., 11:287;
Wagner et al. (1991) Bioconjugate Chemistry 2:226–231;
Wang et al (1997) J Biol Chem 272:22771–22775;
Watson and Akil (1999) Biol Psychiatry 45:533–543;
Webster, et al (1993) Mol Cell Biol 13:2031–2040;
Wu and Wallace (1989) Genomics 4:560;
Yuen et al. (1999) Clin Cancer Res 5:3357–3363;
Young (2000) Cell 102:9–15;
Zaccolo et al. (2000) Nat Cell Biol 2:25–29;
Zang et al. (1997) J Biol Chem 272:13275–13280;
Zenke et al. (1990) Proc Natl Acad Sci USA 87:3655–3659;
Zhu H et al. (1998) Proc Natl Acad Sci U.S.A. 95(24): 14470–5;
Zimmerman et al. (1999) J Biol Chem 274:5370–5378;
Zlokarnik et al. (1998) Science 279:84–88
U.S. Pat. No. 4,683,195
U.S. Pat. No. 4,683,202
U.S. Pat. No. 4,965,188
U.S. Pat. No. 5,352,605
U.S. Pat. No. 5,584,807
U.S. Pat. No. 5,618,682
U.S. Pat. No. 5,674,713
U.S. Pat. No. 5,976,796;
U.S. Pat. No. 6,074,859; and
WO 95/14098.

---

What is claimed is:

1. A method of transfecting a eukaryotic cell, comprising:
   a) providing:
      i) a transfection complex immobilized on a surface, said complex comprising a nucleic acid and first, second, and third complexing agents, said first complexing agent comprising a ligand for a receptor, said second complexing agent comprising a DNA binding molecule, and said third complexing agent comprising a membrane permeable molecule, wherein said membrane permeable molecule is a cationic lipid; wherein said DNA binding molecule is covalently linked to said ligand for a receptor; and
      ii) a eukaryotic cell; and
   b) contacting the cell with the nucleic acid in the transfection complex under conditions such that the cell is transfected.

2. The method of claim 1, wherein the DNA-binding molecule is a cationic protein.

3. The method of claim 1 wherein the transfection complex further comprises one or more cationic lipids.

4. The method of claim 3, wherein the ligand is transferrin and the DNA-bindinag molecule is polylysine.

5. The method of claim 1, wherein the transfection complex further comprises one or more additional complexing agents selected from the group consisting of targeting molecules, transcription molecules, nucleic acid degradation inhibitors, cell growth and integrity modulators, and mixtures thereof.

6. The method of claim 1, further comprising the step of expressing the nucleic acid in the transfected cell.

7. The method of claim 6, further comprising the step of detecting the expression of the nucleic acid in the transfected cell.

8. A method of transfecting a eukaryotic cell, comprising
   a) immobilizing a transfection complex on a surface, said complex comprising a nucleic acid and first, second and third complexing agents, said first complexing agent comprising a ligand for a receptor, said second complexing agent comprising a DNA binding molecule and said third complexing agent comprising a membrane permeable molecule, wherein said membrane permeable molecule is a cationic lipid; wherein said DNA binding molecule is covalently linked to said ligand for a receptor; and
   b) contacting the eukaryotic cell with the immobilized nucleic acid in the transfection complex under conditions sufficient to transfect the cell.

9. A method of transfecting a eukaryotic cell, comprising:
   a) combining a nucleic acid with first, second and third complexing agents, said first complexing agent comprising a ligand for a receptor, said second complexing agent comprising a DNA binding molecule, and said third complexing agent comprising a membrane permeable molecule, wherein said membrane permeable molecule is a cationic lipid, so as to form at least one transfection complex comprising nucleic acid and said first and second complexing agent; wherein said DNA binding molecule is covalently linked to said ligand for a receptor;
   b) immobilizing said transfection complex on a surface so as to form immobilized nucleic acid; and
   c) contacting said eukaryotic cell with said immobilized nucleic acid in said transfection complex under conditions such that said cell is transfected.

10. A method of transfecting a eukaryotic cell, comprising:
   a) covalently linking transferrin to polylysine to form a transferrin-polylysine complex;
   b) combining a nucleic acid and a cationic lipid with said covalently linked transferrin-polylysine complex to form at least one transfection complex;
   c) immobilizing said transfection complex on a surface so as to form immobilized nucleic acid;
   d) contacting said eukaryotic cell with said immobilized nucleic acid in said transfection complex under conditions such that said cell is transfected.

11. A transfection complex comprising a nucleic acid and first, second and third complexing agents, said first complexing agent comprising a ligand for a receptor, said second complexing agent comprising a DNA binding molecule and said third complexing agent comprising a membrane permeable molecule, wherein said membrane permeable molecule is a cationic lipid, wherein said DNA binding molecule is covalently linked to said ligand for a receptor; and wherein said transfection complex is immobilized to a surface.

12. The transfection complex of claim 11, wherein the DNA-binding molecule is a cationic protein.

13. The transfection complex of claim 11, wherein the ligand is transferrin and the DNA-binding molecule is polylysine.

14. The transfection complex of claim 11 further comprising one or more cationic lipids.

15. The transfection complex of claim 11, further comprising at least one additional complexing agent selected from the group consisting of targeting molecules, transcription molecules, nucleic acid degradation inhibitors, cell growth and integrity modulators, and mixtures thereof.

16. A method of transfecting a eukaryotic cell, comprising:
 a) providing:
  i) a transfection complex immobilized on a surface, said complex comprising a nucleic acid and first, second, and third complexing agents, said first complexing agent comprising a ligand for a receptor, said second complexing agent comprising a DNA binding molecule, and said third complexing agent comprising a membrane permeable molecule, wherein said membrane permeable molecule is a cationic lipid; wherein said DNA binding molecule is covalently linked to said ligand for a receptor; and
  ii) a eukaryotic cell; and
 b) contacting the cell with the immobilized transfection complex on the surface under conditions such that the cell is transfected by an active transport process.

17. A transfection complex comprising a nucleic acid, a cationic lipid, a ligand for a receptor and a DNA binding protein, wherein the ligand is a viral protein and wherein the viral protein is covalently bound to the DNA binding protein, and wherein said transfection complex is immobilized on a surface.

18. The transfection complex of claim 17, wherein the viral protein is selected from the group consisting of penton protein, HIV protein GP120, equine rhinitis A virus protein VP1, human adenovirus protein E3, and Epstein-Barr virus protein GP350.

19. The transfection complex of claim 17, wherein the viral protein is penton protein.

20. The transfection complex of claim 17, wherein the DNA-binding protein is selected from the group consisting of polylysine and a histone.

21. The transfection complex of claim 17, wherein the cationic lipid is lipofectamine.

* * * * *